(12) United States Patent
Fu

(10) Patent No.: US 9,963,461 B2
(45) Date of Patent: May 8, 2018

(54) PHILLYGENIN IBUPROFEN ESTER, PREPARATION METHOD THEREFOR, AND APPLICATION THEREOF

(71) Applicant: Li Fu, Dalian (CN)

(72) Inventor: Li Fu, Dalian (CN)

( * ) Notice: Subject to any disclaimer, the term of this patent is extended or adjusted under 35 U.S.C. 154(b) by 0 days. days.

(21) Appl. No.: 15/502,268

(22) PCT Filed: Dec. 23, 2014

(86) PCT No.: PCT/CN2014/094693
§ 371 (c)(1),
(2) Date: Feb. 7, 2017

(87) PCT Pub. No.: WO2016/019683
PCT Pub. Date: Feb. 11, 2016

(65) Prior Publication Data
US 2017/0233403 A1  Aug. 17, 2017

(30) Foreign Application Priority Data
Aug. 7, 2014 (CN) .......................... 2014 1 0387045

(51) Int. Cl.
*C07D 493/04* (2006.01)
(52) U.S. Cl.
CPC .................. *C07D 493/04* (2013.01)
(58) Field of Classification Search
CPC .................................................... C07D 493/04
See application file for complete search history.

(56) References Cited

U.S. PATENT DOCUMENTS 4,150,137 A    4/1979 Noda et al.

FOREIGN PATENT DOCUMENTS

CN         1597656 A       3/2005

*Primary Examiner* — Noble E Jarrell
*Assistant Examiner* — John S Kenyon
(74) *Attorney, Agent, or Firm* — Greer, Burns & Crain, Ltd.

(57) ABSTRACT

The present invention provides a pharmaceutical compound of phillygenin ibuprofen ester as represented by formula (I), preparation method thereof, and applications thereof in anti-virus, antipyresis, anti-inflammation, analgesia and the like:

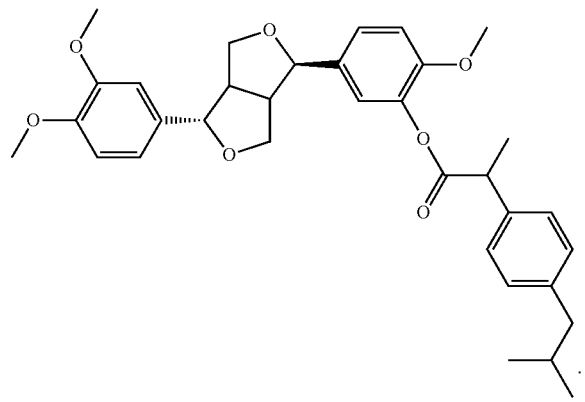

17 Claims, 4 Drawing Sheets

PHILLYGENIN IBUPROFEN ESTER, PREPARATION METHOD THEREFOR, AND APPLICATION THEREOF

This application is the U.S. National phase application corresponding to PCT/CN2014/094693 which was assigned an international filing date of Dec. 23, 2014 and associated with publication WO 2016/019683 A1 and which claims priority to Chinese Application 201410387045.9 filed on Aug. 7, 2014, the disclosures of which are expressly incorporated herein.

TECHNICAL FIELD

The present invention belongs to the field of pharmaceutical chemistry, and specifically, the present invention relates to a preparation method for phillygenin ibuprofen ester as well as the antiviral, antipyretic, anti-inflammatory and analgesic pharmacological effects of such compound.

BACKGROUND ART

Phillygenin, also referred to as phillygenol, is the aglycone portion of phillyrin. It is the main active ingredient of the plant species Forsythia suspensa (Thunb.) Vahlof the genus Forsythia of the family Oleaceae, the structure of which is represented by formula (II). Modern pharmacological studies indicate that phillygenin has the effects of anti-virus, anti-oxidation, blood lipid reducing, free radical clearing, anti-bacteria, anti-tumor, anti-inflammation and the like.

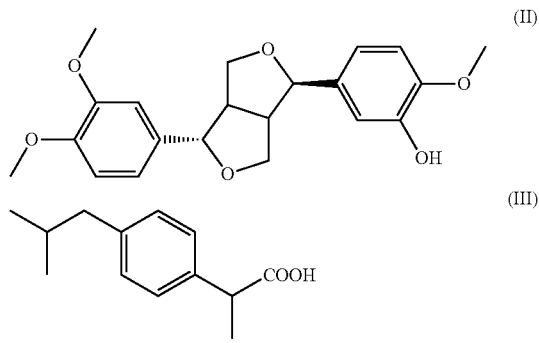

Phillygenin molecules are unstable and easily oxidized, and the molecular configuration is susceptible to change in the acidic environment. It has been found that the phillygenin molecules are extremely easily metabolized into new metabolites by the intestinal flora through the study of phillyrin metabolism simulated by the rat intestinal bacteria.

Ibuprofen is a non-steroidal anti-inflammatory and analgesic effective medicine, the structure of which is represented by formula (III), but a long-term medication will cause such side effects as dyspepsia, gastric ulcer, and liver toxicity and the like. In 1989, Angelini company of Italy developed and marketed an ibuprofen guaiacol ester synthesized from ibuprofen and guaiacol, and the ibuprofen guaiacol ester does not degrade in the human gastrointestinal tract, but is decomposed into ibuprofen and guaiacol after entering the blood, remains to exert antipyretic, analgesic, and anti-inflammatory effects of ibuprofen in vivo, and meanwhile reduces its irritation on the gastrointestinal tract and reduces the liver toxicity. In 2004, Xiuli Zhao of Shenyang Pharmaceutical University carried out the esterification of ibuprofen with eugenol to obtain a pharmaceutical compound of eugenol ibuprofen ester, which also has antiviral, antipyretic, analgesic, anti-inflammatory effects in vivo. Moreover the pharmaceutical compound of eugenol ibuprofen ester has improved the stability of eugenol (Chinese Patent Publication No. CN1597656A).

Hitherto, the reports and records on the synthesis of the ester compound from phillygenin and the pharmacological activities have not yet been found, and therefore we have obtained the phillygenin ibuprofen ester through the esterification reaction of phillygenin with ibuprofen and expect to obtain a new compound which is more stable and has various pharmacological effects of anti-virus, antipyresis, anti-inflammation, and analgesia and the like.

SUMMARY OF THE INVENTION

The purpose of the present invention is to provide a new anti-viral compound of phillygenin ibuprofen ester, a preparation method therefor and applications thereof in view of the existing problems in the above prior arts, and the phillygenin ibuprofen ester provided by the present invention has antiviral, antipyretic, analgesic, and anti-inflammatory effects, and can be used to prepare the medicines or health products for the treatment of anti-virus, antipyresis, and analgesia; the preparation method for phillygenin ibuprofen ester is simple and convenient for operation, and is suitable for industrial scale production.

To achieve the purpose of the present invention, in one aspect the present invention provides a phillygenin ibuprofen ester compound with a general structural formula as represented by formula (I):

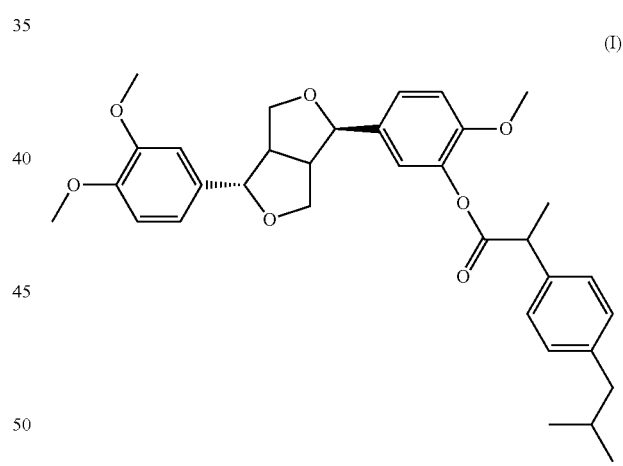

In another aspect, the present invention provides a preparation method for the phillygenin ibuprofen ester compound, comprising the steps conducted according to the following sequence:
A) ibuprofen is subjected to an acylation reaction with an acylating agent to prepare ibuprofen acyl chloride;

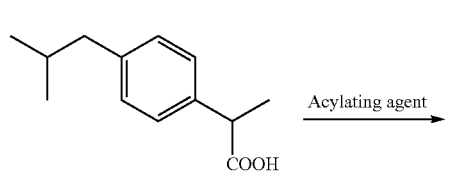

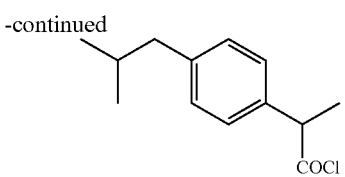

and B) an esterification reaction is carried out between phillygenin and ibuprofen acyl chloride in the presence of a catalyst to obtain the product.

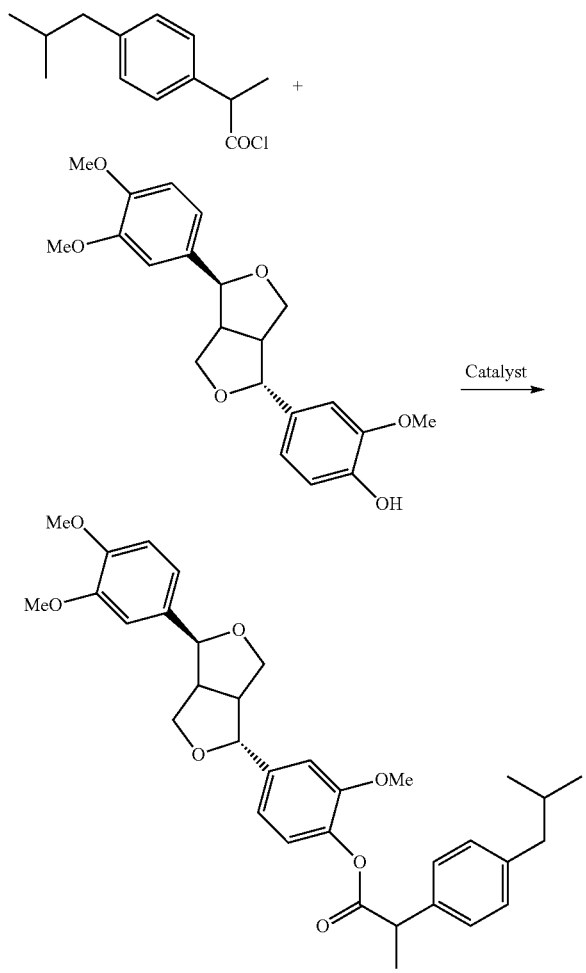

Therein, the acylating agent in step A) is selected from thionyl chloride, phosphorus trichloride, phosphorus pentachloride, phosphorus oxychloride or phosphorus oxypentachloride.

In particular, the reaction temperature of the acylation reaction is 10-30°C.

In particular, the molar ratio of ibuprofen to the acylating agent is 1:10-1:12, preferably 1:10.

In particular, the reaction time is 12 h to 24 h, preferably 15 h to 24 h.

In particular, firstly ibuprofen is dissolved in an organic solvent, and then mixed with the acylating agent, and then the acylation reaction is carried out.

Therein, the amount of the organic solvent used is that every 1 mol of ibuprofen is dissolved in 3 L to 4 L of the organic solvent, preferably 4 L of the organic solvent.

In particular, the organic solvent is selected from toluene, benzene, acetone, dichloromethane, and trichloromethane, preferably dichloromethane and acetone, and more preferably dichloromethane.

In particular, the preparation method further comprises a concentration treatment of the mixture after the acylation reaction in a vacuum state and removal of the organic solvent to obtain the ibuprofen acyl chloride.

In particular, an evaporation treatment is carried out under reduced pressure to remove the organic solvent.

Therein, the catalyst in step B) is selected from an organic base or an inorganic base.

In particular, the ratio of phillygenin to the catalyst is 1:1 to 1.2:1, preferably 1:1.

Therein, the inorganic base is selected from sodium carbonate, potassium carbonate, sodium bicarbonate or potassium bicarbonate; the organic base is selected from pyridine, triethylamine, N,N-dimethylformamide or a metal alkoxide.

In particular, the metal alkoxide is selected from sodium methanolate or potassium tert-butoxide.

Therein, the mole ratio of phillygenin in step B) to ibuprofen in step A) is 0.8:1 to 1.2:1, preferably 1:1.

In particular, the temperature of the esterification reaction is 30° C. to 70° C., preferably 40° C. to 60° C.; the reaction time of the esterification reaction is 12 h to 24 h, preferably 15 h to 20 h.

Therein, the esterification reaction in step B) is carried out in a heating state after phillygenin and ibuprofen acyl chloride are added to the organic solvent.

In particular, the organic solvent is selected from toluene, benzene, acetone, dichloromethane, and trichloromethane, preferably dichloromethane or acetone.

In particular, firstly phillygenin is dissolved in the organic solvent; subsequently the catalyst is added and the mixture is mixed uniformly; then ibuprofen acyl chloride prepared in step A) is added into the uniformly mixed mixture, and the esterification reaction is carried out in the state of stirring and heating.

In particular, the organic solvent is selected from toluene, benzene, acetone, dichloromethane, and trichloromethane, preferably dichloromethane or acetone.

In particular, the amount of the organic solvent used is that every 1 mol of phillygenin is dissolved in 15 L to 25 L of the organic solvent, preferably 20 L of the organic solvent.

In particular, the preparation method further comprises a step C), wherein the product after the esterification reaction is subjected to the isolation and purification treatment: C-1) the mixture after the esterification reaction is cooled and the temperature decreases; C-2) subsequently the mixture is subjected to the filter treatment, the filtrate is subjected to the concentration treatment, and the solvent is removed; C-3) then the solid substance after the organic solvent is removed is subjected to the recrystallization treatment to obtain phillygenin ibuprofen ester.

Therein, the mixture after the esterification reaction in step C-1) is cooled down to 20° C. to 30° C.; the concentration treatment in step C-2) is to evaporate the cooled mixture in a vacuum state to remove the organic solvent; the solvent of the recrystallization treatment in step C-3) is petroleum ether or hexane.

The compound of the present invention prepared by the above-mentioned method is phillygenin ibuprofen ester, which is a white solid at room temperature. The structure of phillygenin ibuprofen ester is confirmed and analyzed as follows:

High resolution mass spectrum: 583.26663; $C_{34}H_{40}O_7Na^{+1}$;

Infrared absorption spectrum: characteristic absorption peak (cm$^{-1}$) 2953.73 (—CH$_3$); 2867.21 (—CH$_2$—); 29835.45 (Ar—OCH$_3$); 1760.11 (C=O); 1606.25, 1591.38, 1514.46 (Ar—CH); and 1270.57, 1042.86 (Ar—O—C).

$^1$H-NMR: (CDCl$_3$, 600 MHz) δppm: 6.856-6.961 (m, 6H), 7.135-7.145 (m, 2H), 7.322-7.335 (d, 2H, J=7.8 Hz), 4.860-4.853 (d, 1H, J=4.2 Hz), 4.494-4.484 (d, 1H, J=6 Hz), 4.145-4.129 (d, 1H, J=9.6 Hz), 3.988-3.976 (d, 1H, J=7.2 Hz), 3.900-3.843 (s, 8H), 3.720-3.713 (s, 3H), 3.346-3.323 (s, 2H), 2.891-2.881 (d, 1H, J=6 Hz), 2.481-2.470 (d, 2H, J=6.6 Hz), 1.882-1.860 (s, 1H), 1.620-1.609 (d, 3H, J=6.6 Hz), 0.920-0.910 (s, 6H).

$^{13}$C-NMR: (CDCl$_3$, 125 MHz) δppm: 172.901(C-28), 151.374(C-12), 148.880(C-18), 148.056(C-13), 140.635(C-35), 140.203(C-17), 139.486 (C-10), 137.436(C-9), 130.971 (C-31), 129.328(C-33), 127.445(C-36), 127.445(C-37), 122.578(C-34), 118.045(C-20), 117.767(C-16), 111.097(C-15), 110.035(C-14), 110.015(C-19), 109.020(C-11), 87.345 (C-6), 82.043(C-4), 71.107(C-1), 69.830(C-8), 55.958(C—OMe), 55.933(C—OMe), 55.851(C—OMe), 54.694(C-2), 50.101(C-3), 45.107(C-38), 45.040(C-30), 30.252(C-39), 22.448(C-40, 41), 18.803(C-32).

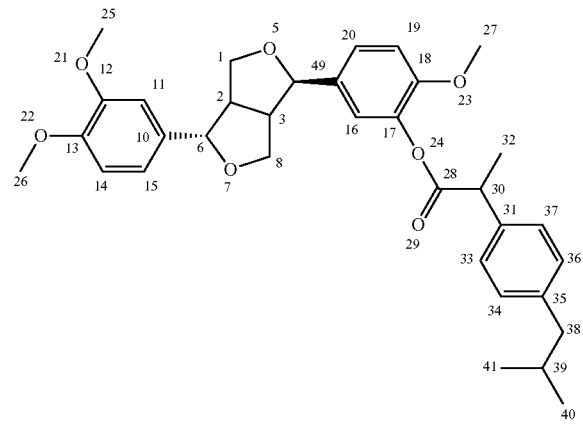

In still another aspect, the present invention provides an antiviral application of phillygenin ibuprofen ester.

In yet another aspect, the present invention provides applications of phillygenin ibuprofen ester in preparation of antiviral drugs or health products.

The present invention also provides applications of phillygenin ibuprofen ester in preparation of antipyretic, analgesic, and anti-inflammatory drugs or health products.

Therein, the present invention provides a pharmaceutical or health product composition which contains phillygenin ibuprofen ester and has antiviral, antipyretic, analgesic, anti-inflammatory efficacies.

In particular, the pharmaceutical composition comprises phillygenin ibuprofen ester of the present invention, and pharmaceutically acceptable excipients.

Herein, the pharmaceutically acceptable excipients refer to non-toxic solid, semi-solid or liquid fillers, diluents, carriers, pH regulators, ionic strength adjustors, extended-release or controlled-release agents, encapsulating materials or other pharmaceutical excipients. The carrier used may be adapted to the corresponding administration method, and can be formulated into injections, lyophilized powders (for injection), sprays, oral solutions, oral suspensions, tablets, capsules, gastro-resistant tablets, pills, powders, granules, sustained-release or delayed-release formulations and the like with the excipients which are well known to those skilled in the art. Preferably, phillygenin ibuprofen ester of the first aspect of the present invention is administered by way of injection or through the digestive tract, and therefore, the pharmaceutical composition of the present invention is preferably an injection or a formulation through the digestive tract administration, i.e. the excipients adapted for being formulated to administration by way of injection or through the digestive tract are particularly preferred. Therein, "administration through the digestive tract" herein refers to an approach of administrating medicine formulations through the patient's digestive tract, including oral administration, intragastric administration, and enema administration and the like, preferably oral administration, for example, excipients which are well known to those skilled in the art can be used to formulate into oral solutions, oral suspensions, tablets, capsules, enteric tablets, pills, powders, granules, sustained-release or delayed-release preparations and the like; wherein the injection preparations are mainly injections and powder-injections.

The new compound of phillygenin ibuprofen ester of the present invention has antiviral, antipyretic, analgesic and anti-inflammatory efficacies, and can be used for preparing antiviral, antipyretic, analgesic, anti-inflammatory drugs or health products; phillygenin ibuprofen ester is prepared by the esterification reaction, and the preparation method has the advantages of mild reaction condition, high yield, low energy consumption, environmental friendliness, easily controlled operation process conditions, and strong quality controllability, and is suitable for industrial large-scale productions.

In the above mentioned esterification reaction, phillygenin is dissolved in a suitable organic solvent, and ibuprofen acyl chloride is added into the reaction system to carry out the esterification reaction for 10 h to 24 h. After the reaction is stopped, the reaction liquid is washed with water until neutral, a desiccant is added to remove the water finally, the organic solvent is evaporated under reduced pressure to obtain a white solid, and the resulting solid is recrystallized to obtain phillygenin ibuprofen ester.

DETAILED DESCRIPTION OF THE INVENTION

Figure 1:
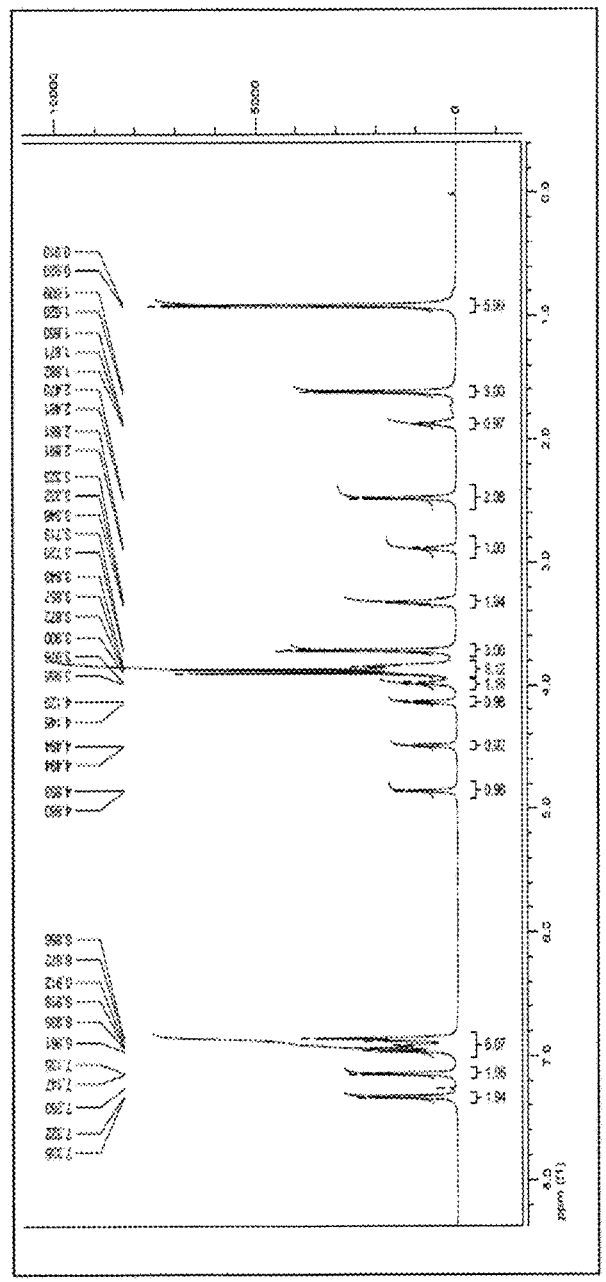
FIG. 1 is the $^1$H-NMR spectrum of phillygenin ibuprofen ester of the present invention.

The present invention will be further described through the following examples. However, these examples are only illustrative of the present invention, and should not be construed as any limitation to the scope of the present invention. In addition, the reagents and the raw materials in the examples can be obtained from commercial sources, and for more details, you can refer to organic synthesis guidelines, guidelines of drug supervision and administration agencies, and manufacturer's instructions of the corresponding apparatuses and reagents and the like.

EXAMPLE 1

1. Acylation Reaction

Ibuprofen (2.06 g, 0.01 mol) was fed into a three-necked flask, and dissolved in 40 mL of dichloromethane; an acylation reagent of thionyl chloride (11.9 g, 0.1 mol) was added into the three-necked flask, the reaction was carried out at room temperature (20° C.) for 15 h, and dichloromethane was evaporated with a reduced pressure (i.e., under the condition of vacuum) to obtain ibuprofen acyl chloride, wherein the molar ratio of ibuprofen to the acylating agent was 1:10;

2. Esterification

Phillygenin (3.72 g, 0.01 mol) was placed into a three-necked flask containing 200 ml of the acetone, and the mixture was mixed uniformly; consequently the catalyst of potassium carbonate (1.5 g, 0.01 mol) was added, and the mixture was stirred uniformly; then ibuprofen acyl chloride (2.24 g, 0.01 mol) prepared in step 1) was added dropwise into the three-necked flask; the mixture was heated to 60° C. while stirring, and the esterification reaction was carried out for 15 h while maintaining the temperature of 60° C.;

3. Isolation and Purification Treatment

The resulting mixture after the esterification reaction was cooled to room temperature (20° C.-25° C.), the mixture was filtered, the solid residue was removed, and the filtrate was evaporated with a reduced pressure to recover the acetone solvent and solid residue was obtained;

the resulting solid after the solvent was recovered was dissolved in dichloromethane, the resulting solution was washed with water until neutral and dried with anhydrous sodium sulfate, and the dichloromethane solvent was evaporated under the condition of vacuum (i.e., reduced pressure) to obtain a white solid.

The resulting white solid was subjected to the recrystallization treatment with petroleum ether to obtain phillygenin ibuprofen ester (5.49 g) with a yield of 98%.

Phillygenin ibuprofen ester is a white solid, melting point: 110° C.; solubility: soluble in methanol; chloroform, and dichloromethane and the like.

High resolution mass spectrum: 583.26663 $C_{34}H_{40}O_7Na^{+1}$; molecular weight: 561.

Figure 3:
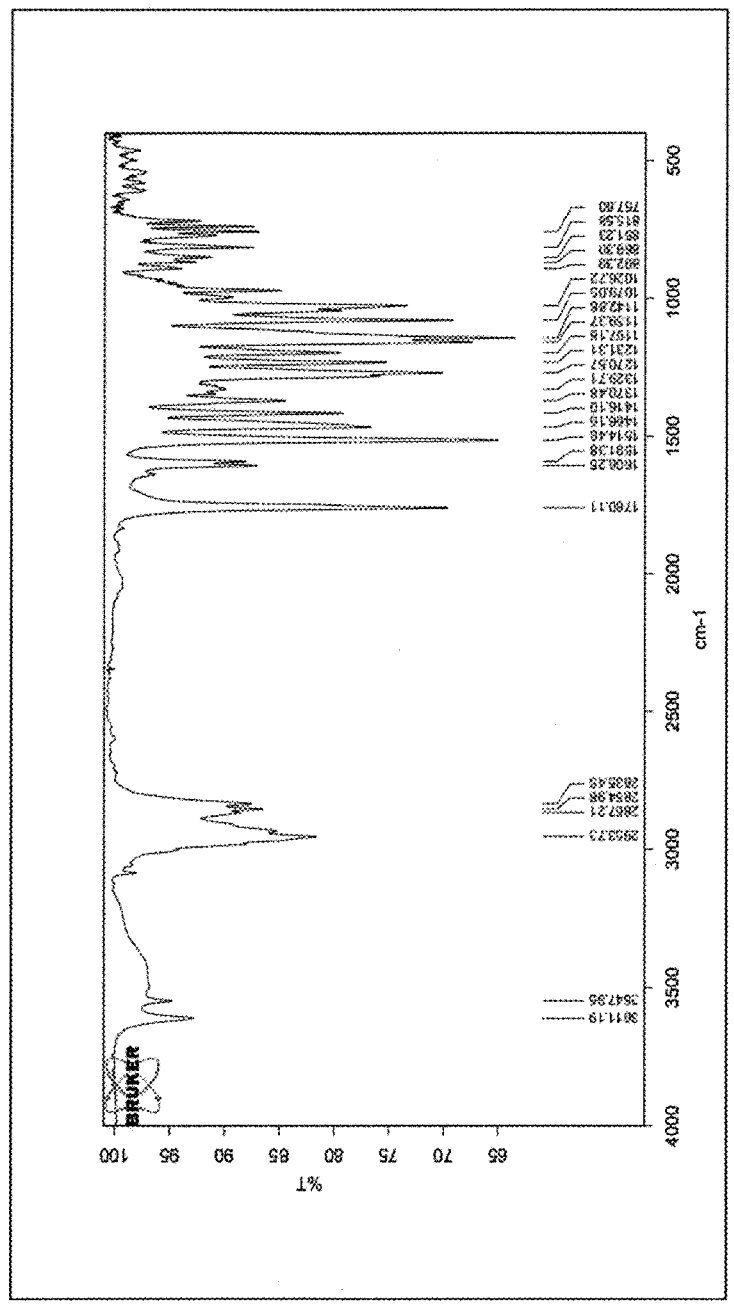
FIG. 3 is the infrared (IR) absorption spectrum of phillygenin ibuprofen ester of the present invention.

Infrared absorption spectrum: characteristic absorption peak (cm$^{-1}$) 2953.73 (—CH$_3$); 2867.21 (—CH$_2$—); 29835.45 (Ar—OCH$_3$); 1760.11 (C=O); 1606.25, 1591.38, 1514.46 (Ar—CH); 1270.57, 1042.86 (Ar—O—C), as shown in FIG. 3.

$^1$H-NMR: (CDCl$_3$, 600 MHz) δppm: 6.856-6.961 (m, 6H), 7.135-7.145 (m, 2H), 7.322-7.335 (d, 2H, J=7.8 Hz), 4.860-4.853 (d, 1H, J=4.2 Hz), 4.494-4.484 (d, 1H, J=6 Hz), 4.145-4.129 (d, 1H, J=9.6 Hz), 3.988-3.976 (d, 1H, J=7.2 Hz), 3.900-3.843 (s, 8H), 3.720-3.713 (s, 3H), 3.346-3.323 (s, 2H), 2.891-2.881 (d, 1H, J=6 Hz), 2.481-2.470 (d, 2H, J=6.6 Hz), 1.882-1.860 (s, 1H), 1.620-1.609 (d, 3H, J=6.6 Hz), 0.920-0.910 (s, 6H), as shown in FIG. 1.

Figure 2:
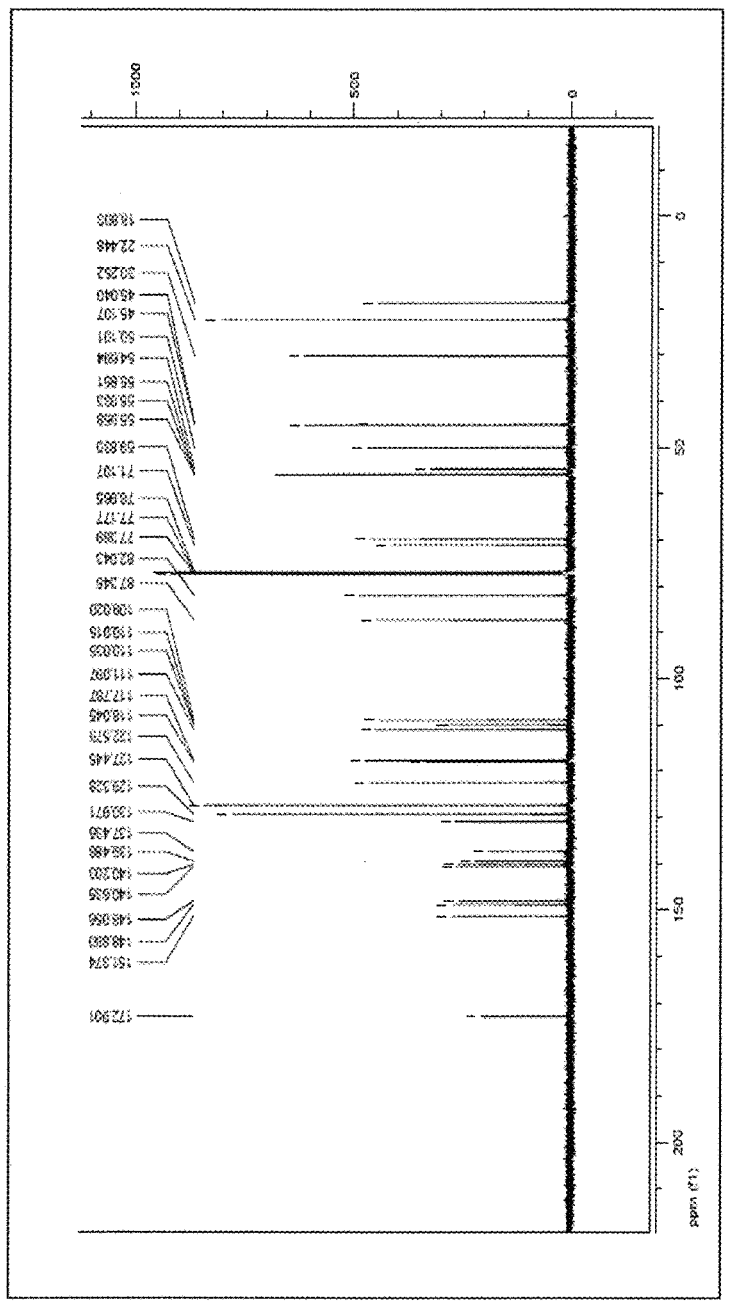
FIG. 2 is the $^{13}$C-NMR spectrum of phillygenin ibuprofen ester of the present invention.

$^{13}$C-NMR: (CDCl$_3$, 125 MHz) δppm: 172.901(C-28), 151.374(C-12), 148.880(C-18), 148.056(C-13), 140.635(C-35), 140.203(C-17), 139.486 (C-10), 137.436(C-9), 130.971 (C-31), 129.328(C-33), 127.445(C-36), 127.445(C-37), 122.578(C-34), 118.045(C-20), 117.767(C-16), 111.097(C-15), 110.035(C-14), 110.015(C-19), 109.020(C-11), 87.345 (C-6), 82.043(C-4), 71.107(C-1), 69.830(C-8), 55.958(C—OMe), 55.933(C—OMe), 55.851(C—OMe), 54.694(C-2), 50.101(C-3), 45.107(C-38), 45.040(C-30), 30.252(C-39), 22.448(C-40, 41), 18.803(C-32), as shown in FIG. 2.

EXAMPLE 2

1. Acylation Reaction

Ibuprofen (2.06 g, 0.01 mol) was fed into a three-necked flask, and dissolved in 40 mL of dichloromethane; the acylation reagent of phosphorus oxychloride (15.3 g, 0.1 mol) was added into the three-necked flask, the reaction was carried out at room temperature (30° C.) for 15 h, and dichloromethane was evaporated with a reduced pressure (i.e., under the condition of vacuum) to obtain ibuprofen acyl chloride, wherein the molar ratio of ibuprofen to the acylating agent was 1:10;

2. Esterification Reaction

Phillygenin (3.72 g, 0.01 mol) was placed into a three-necked flask containing 200 ml of a dichloromethane solvent, and the mixture was mixed uniformly; consequently the catalyst of triethylamine (1.5 ml, 0.01 mol) was added, and the mixture was stirred uniformly; then ibuprofen acyl chloride (2.24 g, 0.01 mol) prepared in step 1) was added dropwise into the three-necked flask; the mixture was heated to 40° C. while stirring, and the esterification reaction was carried out for 20 h while maintaining the temperature of 40° C.;

3. Isolation and Purification Treatment

The resulting mixture after the esterification reaction was cooled to room temperature (20° C.-25° C.), the mixture was filtered, the solid residue was removed, and the filtrate was evaporated with a reduced pressure to recover the dichloromethane solvent and solid residue was obtained;

the resulting solid after the solvent was recovered was dissolved in dichloromethane, the resulting solution was washed with water until neutral and dried with anhydrous sodium sulfate, and the dichloromethane solvent was evaporated under the condition of vacuum (i.e., reduced pressure) to obtain a white solid.

The resulting white solid was subjected to the recrystallization treatment with petroleum ether to obtain phillygenin ibuprofen ester (5.44 g) with a yield of 97%.

The physicochemical properties, spectral data and mass spectral data of the white solid obtained by the recrystallization were consistent with those of phillygenin ibuprofen ester prepared in Example 1.

EXAMPLE 3

1. Acylation Reaction

Ibuprofen (2.06 g, 0.01 mol) was fed into a three-necked flask, and dissolved in 40 mL of dichloromethane; the acylation reagent of phosphorus oxypentachloride (20.8 g, 0.1 mol) was added into the three-necked flask, the reaction was carried out at room temperature (10° C.) for 15 h, and dichloromethane was evaporated with a reduced pressure (i.e., under the condition of vacuum) to obtain ibuprofen acyl chloride, wherein the molar ratio of ibuprofen to the acylating agent was 1:10;

2. Esterification Reaction

Phillygenin (3.72 g, 0.01 mol) was placed into a three-necked flask containing 200 ml of a trichloromethane solvent, and the mixture was mixed uniformly; consequently the catalyst of sodium methoxide (1.5 ml, 0.01 mol) was added, and the mixture was stirred uniformly; then ibuprofen acyl chloride (2.24 g, 0.01 mol) prepared in step 1) was added dropwise into the three-necked flask; the mixture was heated to 50° C. while stirring, and the esterification reaction was carried out for 17 h while maintaining a temperature of 50° C.;
3. Isolation and Purification Treatment The resulting mixture after the esterification reaction was cooled to room temperature (20° C.-30° C.), the mixture was filtered, the solid residue was removed, and the filtrate was evaporated with a reduced pressure to recover the trichloromethane solvent and solid residue was obtained;

The resulting solid after the solvent was recovered was dissolved in dichloromethane, the resulting solution was washed with water until neutral and dried with anhydrous sodium sulfate, and the solvent of dichloromethane was evaporated under the condition of vacuum (i.e., reduced pressure) to obtain a white solid.

The resulting white solid was subjected to the recrystallization treatment with petroleum ether, to obtain phillygenin ibuprofen ester (5.49 g) with a yield of 98%.

The physicochemical properties, spectral data and mass spectral data of the white solid obtained by the recrystallization were consistent with those of phillygenin ibuprofen ester prepared in Example 1.

TEST EXAMPLE 1

Antiviral Test of phillygenin ibuprofen ester

1 In Vitro Antiviral Test
1.1 Test Materials
(1) Drugs
① phillygenin ibuprofen ester: a white solid (prepared in Example 1), manufactured by Dalian Fusheng Natural Drug Development Co., Ltd., and determined by two high performance liquid chromatography detectors, i.e., the ultraviolet detector and evaporative light-scattering detector, through the area normalization method; and the purities thereof is 99.1%.
② ribavirin injection: a colorless and transparent solution, manufactured by Henan Runhong Co., Ltd., and the product lot number is (lot No.): 1206261, National medical Permitment No.: H19993553, 100 mg/ml, adopted as the positive control drug for the present test;
③ oseltamivir phosphate: available from National Institute for Control of Pharmaceutical & Biological Products, with Batch No. 101096-200901; 100 mg/each, adopted as the positive control drug for the present test;
④ phillygenin: a white powder, manufactured by Dalian Fusheng Natural Drug Development Co., Ltd., and determined by two high performance liquid chromatography detectors, i.e., the ultraviolet detector and evaporative light-scattering detector, through the area normalization method; and the purities thereof is 99.1%.
⑤ ibuprofen: purchased from National Institute for Control of Pharmaceutical and Biological Products, with Batch No.: 0179-9702.

The above-mentioned drugs were all dissolved with purified water, filtered, sterilized, subpackaged, and stored at 4° C. for standby application; all of them were drugs to be tested in the present test.
(2) Cell Strain
cell strain of Vero (African green monkey kidney cells) was preserved by College of Basic Medical Sciences of Jilin University.
(3) Virus Strains
① influenza virus, parainfluenza virus, respiratory syncytial virus (RSV): purchased from the Virology Institute of Chinese Academy of Preventive Medicine;
② coxsackie virus B3 (CVB3): purchased from Wuhan Institute of Virology, Chinese Academy of Sciences;
③ Coxsackie virus A16 (CoxA16) and Enterovirus EV71: purchased from Sendai National Hospital of Japan;
④ Adenovirus (AdV): purchased from Pediatric Research department of The First Hospital of Norman Bethune Medical University;
⑤ Herpes Simplex Virus type I (HSV-1): purchased from National Institute for the Control of Pharmaceutical and Biological Products, Ministry of Health.
(4) Main Equipments and Reagents
Biological safe cabinet: BHC-1300 II A/B3, AIRTECH;
$CO_2$ incubator: MCO-18AIC, SANYO;
Inverted microscope: CKX41, OLYMPUS;
Electronic analytical balance: AR1140/C, DHAUS;
Culture medium: DMEM, HyClone;
Fetal bovine serum: HyClone;
Trypsin: Gibco;
MTT: Sigma;
DMSO: Tianjin Beilian Fine Chemicals Development Co., Ltd.
1.2 Test Methods
(1) Cells Preparation
Vero cells were subcultured for 1-2 days to form a film, and when the boundary line was clear and the three-dimensional sense and the diopter were strong, they were digested with the pancreatic enzyme; when there were needle-like wells on the cell surface, the digestive juice was completed drained, and the cells were dispersed with several milliliters of culture medium, counted, and then diluted to about $5\times10^7$ cells/L with the culture medium (DMEM containing 10% fetal bovine serum) and inoculated in a 96-well culture plate until the cells grew into a monolayer.
(2) Determination of the Drug Toxicity
Cytotoxicity test: the drugs were diluted according to the concentrations of table 1-1 for the determination of cytotoxicity.

TABLE 1-1

Drug dilution reference table (unit: g/L)

| drug | concentration gradient | | | | | | | |
|---|---|---|---|---|---|---|---|---|
| | gradient 1 | gradient 2 | gradient 3 | gradient 4 | gradient 5 | gradient 6 | gradient 7 | gradient 8 |
| phillygenin ibuprofen ester | 5 | 2.5 | 1.25 | 0.625 | 0.3125 | 0.15625 | 0.078125 | 0.039063 |
| ribavirin | 5 | 2.5 | 1.25 | 0.625 | 0.3125 | 0.15625 | 0.078125 | 0.039063 |
| oseltamivir phosphate | 2 | 1 | 0.5 | 0.25 | 0.125 | 0.0625 | 0.03125 | 0.015625 |
| phillygenin | 5 | 2.5 | 1.25 | 0.625 | 0.3125 | 0.15625 | 0.078125 | 0.039063 |
| ibuprofen | 5 | 2.5 | 1.25 | 0.625 | 0.3125 | 0.15625 | 0.078125 | 0.039063 |

The above drugs, which were diluted with a maintenance solution (DMEM containing 2% of fetal bovine serum) to different concentrations, were added dropwise to the Vero monolayer cell with 0.2 ml per pore, and for each concentration, the drugs were added in sextuplicate in 6 pores respectively. In addition, 6 pores were set up as normal control (without drugs) while another 6 pores as blank control (medium only). Cells were grown in an incubator at 37° C. under 5% $CO_2$ and CEP was daily observed with inverted microscope and recorded. After 72 hours, 20 μL (5 mg mL$^{-1}$) MTT solution was added into each well and incubated sequentially for 4 hours, the culture medium of each well was sucked and discarded, 100 μL DMSO was added to each well, shaken for 5 minutes, and the OD value was measured at 492 nm to calculate the cell survival rate. In the SPSS 18.0 statistical software, the cell survival rate was subjected to Probit Regression Analysis to calculate the maximal non-toxic concentration ($TC_0$) and median toxic concentration ($TC_{50}$) of the drug against the Vero cell.

(3) Determination of $TCID_{50}$ of Various Viruses

Various viruses were diluted by a 10-fold decrement to have different dilutions of $10^{-1}$, $10^{-2}$, $10^{-3}$, $10^{-4}$, $10^{-5}$. To each of sextuplicate pores of a 96-pore culture plate containing monolayer Vero cells was inoculated 100 μl diluent for each dilution in-sequence while the normal cell control was set up. The plates were incubated for 2 h at 37° C. in 5% $CO_2$ followed by the removal of virus solution, and 100 μL cell maintenance medium was added to each pore for further incubation at 37° C. in 5% $CO_2$. The cytopathic effect was examined under the microscope from the 3rd day on, and the results were determined and recorded on the $7^{th}$-$8^{th}$ day. The virus titer was calculated by karber method with maximal dilution titer that allowed positive cytopathy to occur in 50% of the cell pores as the end point.

Formula:

$$LogTCID_{50} = XM + \frac{1}{2}d - d\frac{\Sigma Pi}{100}$$

$TCID_{50}$: 50% histocyte infection dose
XM: logarithm of the highest concentration dilution of virus
d: logarithm of the dilution coefficient (multiple);
Σpi: the sum of the cytopathy percentages for each dilution;

(4) Impact of the Drugs on the Virus-induced Cytopathy

A culture medium in plates covered with a monolayer cells was sucked and discarded, cells were inoculated at an amount of virus attacking corresponding to 100 $TCID_{50}$, absorbed in an incubator at 37° C. with 5% $CO_2$ for two hours, and then added of specific concentrations (about the maximal non-cytotoxic concentration) of each drug fluid.

Each concentration was performed in sextuplicate in 6 pores with 200 μL/well. Ribavirin injection and oseltamivir phosphate served as positive control groups while normal control group (without virus and drug) and virus control group (adding virus but no drug) were set up to examine the effect of drugs on virus-induced CPE. After 72 hours, the OD value was measured under 492 nm wavelength by using an MTT colorimetric method, and the antiviral effective rate (ER %) of the drugs was calculated. The analysis of variance (ANOVA) method in SPSS 18.0 statistical software was used to determine if there was a significant difference among different drugs groups on antiviral efficiency.

ER %=(the average OD value of the drug-treated group−the average OD value of the virus control group)/(the average OD value of the cell control group−the average OD value of the virus control group)×100%

1.3 Test Results (1) $TCID_{50}$ of Various Viruses parainfluenza virus: $LogTCID_{50} = -2 + 0.5 - \frac{100+100+50}{100} = -4$ influenza virus: $LogTCID_{50} = -2 + 0.5 - \frac{100+100+50}{100} = -4$ $CVB_3$: $LogTCID_{50} = -2 + 0.5 - \frac{100+100+100+50}{100} = -5$ HSV-1: $LogTCID_{50} = -2 + 0.5 - \frac{100+100+100+50}{100} = -4.8$ AdV: $LogTCID_{50} = -2 + 0.5 - \frac{100+100+50}{100} = -4$ RSV: $LogTCID_{50} = -2 + 0.5 - \frac{100+100+100+50}{100} = -5$ CoxA16: $LogTCID_{50} = -2 + 0.5 - \frac{100+100+100+50}{100} = -5$ EV71: $LogTCID_{50} = -2 + 0.5 - \frac{100+100+100+50}{100} = -5$ (2) Determination of the Drug Toxicity 1) Determination of the Cytotoxicity of Drugs The maximal non-toxic concentrations ($TC_0$) and median toxic concentrations ($TC_{50}$) of the drugs on the Vero cell and the concentrations of the drug used for antiviral test were shown in Table 1-2.

TABLE 1-2

Results of drug cytotoxicity test (unit: g/L)

| virus | Phillygenini buprofen | ribavirin | oseltamivir phosphate | phillygenin |
|---|---|---|---|---|
| maximal non-toxic concentration | 0.109 | 0.065 | 0.28 | 0.011 |
| Mediantoxic concentration | 0.485 | 1.392 | 0.832 | 0.297 |
| | 0.30 | 0.03 | 0.70 | 0.30 | 0.02 |

2) Results of Protective Effects of Drugs on the Virus-induced Cytopathy

For the effective rates of the drugs in resisting various viruses and results of the ANOVA-method one-way analysis of variance, see Table 3 for details.

TABLE 1-3

Statistical table of antiviral effective rate (ER %) of drugs

| virus | phillygenin ibuprofen | ribavirin | oseltamivir phosphate | philly-genin | |
|---|---|---|---|---|---|
| influenza viruses | 99.95**# | 57.49* | 81.76** | 55.12* | 75.35** |
| para-influenza virus | 100.00**# | 81.56** | 94.52** | 65.96** | 80.72** |
| CoxA16 | 75.89**## | 0.70 | 2.95 | 1.35 | 50.04 |
| RSV | 87.74**# | 50.08* | 37.60 | 52.33* | 80.88** |
| HSV-I | 99.80**# | 60.92** | 66.56** | 62.10* | 84.30** |

TABLE 1-3-continued

Statistical table of antiviral effective rate (ER %) of drugs

| viruse | drug | | | | | |
|---|---|---|---|---|---|---|
| | phillygenin ibuprofen | ribavirin | oseltamivir phosphate | phillygenin | | |
| ADV | 75.90**## | 0.43 | 10.31 | 5.07 | 50.61 | |
| EV71 | 99.81**## | 4.25 | 51.86 | 9.88 | 75.86** | |
| CVB$_3$ | 75.83**## | 13.44 | 1.64 | 15.02 | 50.89 | |

Note:
compared with the virus control group,
*P < 0.05,
**P < 0.01;
compared with phillygenin,
P < 0.05,
P < 0.01.

As shown in table 1-3, both the inhibitive rate and effective rate of phillygenin ibuprofen ester on the influenza virus, the parainfluenza virus, the Herpes Simplex Virus Type I (HSV-I) and the enterovirus EV71 are greater than 99% with distinct differences compared with the virus control group and are statistically significant.
The antiviral efficacy of phillygenin ibuprofen ester on a number of viruses was superior to that of phillygenin, ribavirin and oseltamivir phosphate.

2. In Vivo Antiviral Test 2.1 Test Materials (1) Test Animals

Kunming mice, Medicinal Animal No. 10-5219, were provided by the Experimental Animal Center of the Norman Bethune Science center of Jilin University.

(2) Detection Instruments and Reagents

| Instrument Name | Model | Manufacturer |
|---|---|---|
| Quantitative PCR Instrument | 7300 | ABI |
| PCR INSTRUMENT | ES-60J | Electronic Analytical Balance |
| Electronic Analytical Balance | FA1004 | Shenyang Longteng Co., Ltd. |
| $CO_2$ Incubator | HG303-5 | Nanjing Experimental Instrument Factory |
| Superclean Bench | SW-CJ-IF | Suzhou Antai Technology Co., Ltd. |
| Inverted microscope | CKX41 | Olympus Instrument |
| −80° C. Ultra-low temperature freezer | TECON-5082 | Australia |
| Water bath oscillator | HZS-H | Harbin Donglian Co., Ltd. |
| Microplate reader | TECAN A-5082 | Australia |
| Spectrophotometer | Model 7550 | Japan |

2.2 Test Method (1) Determination of the Median Lethal Dose of the Mice Due to Influenza Virus and Parainfluenza Virus The influenza virus and the parainfluenza virus (cell lysate) were diluted by a 10-fold decrement into virus liquids with concentrations of 10-1, 10-2, 10-3, 10-4, and 10-5. 120 Kunming mice were adopted, 60 of which were provided for the influenza virus group and the remaining 60 were provided for the parainfluenza virus group, and were randomly divided into 6 groups separately; the mice were lightly anesthetized with ether, and were infected nasally with virus liquids having different dilutions at 0.03 mL/mouse. Meanwhile the blank control was set, and the virus liquid was replaced with saline. Death and survival were used as the observational indexes, and observation was performed every day until 14 days after infection. Those died within 24 hours of infection were nonspecific death and were not counted up, and the virus liquid LD50 was calculated by using the Karber method.

Calculation formula:

$$\text{Log}LD_{50} = XM + \frac{1}{2}d - d\frac{\Sigma Pi}{100}$$

[wherein: $LD_{50}$: median lethal dose; XM: logarithm of the highest concentration dilution of virus; d: logarithm of the dilution coefficient (multiple); $\Sigma pi$: the sum of the each dilution cytopathy percentage].

(2) Research on the Resistance of the phillygenin ibuprofen ester to Pneumonia Caused by Anti-influenza Virus and Parainfluenza Virus Infection 1) Test Animals and Groups Division 840 Four weeks-old Kunming mice were adopted to perform two tests. 420 Mice were adopted and randomly divided into 21 groups (20 for each group) for test of determining lung index and the inhibitory rate of the lung index of phillygenin ibuprofen ester to the mice infected by the influenza virus; the test was repeated for 3 times, 70 mice each time. Additional 420 mice were adopted and randomly divided into 21 groups (20 for each group) for the determination of determining lung suspension virus hemagglutination titer of phillygenin ibuprofen ester; the test was repeated for 3 times, 70 mice each time.

2) Infection Method

A degreasing cotton was placed in a 200-300 mL beaker, and a suitable amount of diethyl ether (just for making cotton wet) was added thereto. The beaker containing the degreasing cotton was inverted upside down, the mice were extremely excited when anesthetized therein, and were made to lie on their backs when clearly weak, the mice were infected nasally with 15LD50 influenza virus and parainfluenza virus at 0.03 ml/nostril, and the virus suspension was replaced with normal saline in the normal control group.

3) Administration Method and Administration Dosage

The mice were administered intragastrically with phillygenin ibuprofen ester group, ribavirin and oseltamivir phosphate before the day when they were infected. The high, medium and low administration doses of phillygenin ibuprofen ester were 13.0, 8.0, and 4.0 mg/kg respectively, the administration dose of the ribavirin was 58.5 mg/kg, once daily for 5 consecutive days, and the mice in the virus control group were administered with normal saline of the same volume.

4) Observational Index

① Lung Index Determination

In the fifth day after drugs are administered by mice, the mice are prevented from drinking water for 8 hours first; then, after the mice are weighed, their eyes are moved and said animals are sacrificed by exsanguination through eye enucleation; Then the lungs were removed after the opening of the chest, washed twice with normal saline followed by removal of the moisture from surface with a filter paper and weighed by using an electronic balance. Lung index and the inhibitory rate of the lung index are calculated according to the following equations:

lung index=(mouse lung weight/mouse body weight)×100%; the inhibitory rate of the lung index=(average lung index of the infection model group−average index of the test group)/average lung index of the infection model group×100%.

② Determination of Lung Suspension Virus Hemagglutination Titer

Various groups of mice lungs were respectively picked on the fifth day after treatment, and were ground into homogenate by a homogenizer at a low temperature; the homogenate was diluted into 10% of lung tissue suspension with normal saline; centrifugation was performed to obtain a supernatant, which was double diluted and then dripped to a titration plate with 0.2 ml/well; 0.2 ml of 1% chicken erythrocyte suspension was added into each well and mixed well; the titration plate was placed in a room temperature environment for 30 minutes to observe and record the hemagglutination titers. The end point appears when the erythrocyte was agglutinated (++), and its titer was expressed by the suspension dilution multiple.

③ Histomorphology Observation of Lung

On Day 5 after treatment, the lungs of mice in each group were picked, and general pathological changes of their viscera are observed by naked eyes and are recorded. The lungs were rinsed with normal saline and moisture thereon is sucked up by using filter paper, a part of the lung was fixed with 10% formaldehyde and embedded with paraffin and sliced, and the lung tissue slices were stained with HE, followed by observation and photographing under a microscope.

2.3 Test Results and Analysis (1) Result of the Median Lethal Dose of the Mice Due to the Influenza Virus and the Parainfluenza Virus Kunming mice in the test groups were respectively infected nasally with 30 μL of the influenza virus and the parainfluenza virus liquids of different concentrations; on the third day of infection, all of the mice in the first three groups ($10^{-1}$ group, $10^{-2}$ group and $10^{-3}$ group based on virus concentrations) experienced disease symptoms of different degrees: pilomotor fur, trembling, degreased appetite and so on; on the fifth day, the mice stumble; on the sixth day, the mice in the group of the highest virus concentration ($10^{-1}$ group) began to die, and death occurred successively in the remaining groups on the seventh day of infection. After the observation of 14 days was complete, the mortality of the mice of each group was counted, and the results were shown in Table 1-4 and Table 1-5 below. By calculation, $LD_{50}$ of the influenza virus was a dilution of $10^{-2.9}$, and $LD_{50}$ of the parainfluenza virus was a dilution of $10^{-2.5}$.

TABLE 1-4

The test results of median lethal dose of the influenza virus

| Influenza virus group | Cumulative mortality | Cumulative survival | Cumulative mortality rate |
|---|---|---|---|
| group $10^{-1}$ | 9 | 1 | 90% |
| group $10^{-2}$ | 7 | 3 | 70% |
| group $10^{-3}$ | 4 | 6 | 40% |
| group $10^{-4}$ | 3 | 7 | 30% |
| group $10^{-5}$ | 1 | 9 | 10% |
| blank group | 0 | 10 | 0% |

The $LD_{50}$ values of viruses were calculated by the Karber method. The Log $LD_{50}$ value of the influenza virus was as follows:

$$LogLD_{50} = XM + \frac{1}{2}d - d\frac{\Sigma Pi}{100} =$$
$$-1 + 0.5 - (80\% + 60\% + 40\% + 20\% + 0\% + 0\%) = -2.9$$

TABLE 1-5

The test results of median lethal dose of the parainfluenza virus

| Influenza virus group | Cumulative mortality | Cumulative survival | Cumulative mortality rate |
|---|---|---|---|
| group $10^{-1}$ | 8 | 2 | 80% |
| group $10^{-2}$ | 6 | 4 | 60% |
| group $10^{-3}$ | 4 | 6 | 40% |
| group $10^{-4}$ | 2 | 8 | 20% |

TABLE 1-5-continued

The test results of median lethal dose of the parainfluenza virus

| Influenza virus group | Cumulative mortality | Cumulative survival | Cumulative mortality rate |
|---|---|---|---|
| group $10^{-5}$ | 0 | 10 | 0% |
| blank group | 0 | 10 | 0% |

The $LD_{50}$ values of viruses were calculated by the Karber method. The Log $LD_{50}$ value of the parainfluenza virus was as follows:

$$LogLD_{50} = XM + \frac{1}{2}d - d\frac{\Sigma Pi}{100} =$$
$$-1 + 0.5 - (90\% + 70\% + 40\% + 30\% + 10\% + 0\%) = -2.5$$

(2) Results of phillygenin ibuprofen ester on Resistance to Pneumonia Caused by the Influenza Virus and the Parainfluenza Virus Infections.

① Lung Index Determination

After the mice were infected with the influenza virus and the parainfluenza virus, the average lung index showed that: compared with the infection model group, phillygenin ibuprofen ester had certain protective effect at the concentration range of 3.25-13.0 mg/kg/d, and all the lung indexes decreased obviously; the therapeutic effects of the high-dose phillygenin ibuprofen ester group against the influenza virus and the parainfluenza virus were much better than the phillygenin group (P<0.05). The results could be seen in Tables 1-6 and 1-7.

TABLE 1-6

Impact of phillygenin ibuprofen ester on the the lung index and the inhibitive rate ofthe lung indexinfluenza virus infected mice (n = 3)

| Groups | | Drug dosage (mg/kg/d) | Lung index ($\bar{X} \pm S$) | Lung index Inhibitive rate (%) | P value |
|---|---|---|---|---|---|
| Normal control group | | 0 | 1.274 ± 0.102 | — | |
| Virus control group | | 0 | 1.488 ± 0.084 | — | |
| Ribavirin group | | 58.5 | 1.281 ± 0.061 | 13.90 | *<0.05 |
| Oseltamivir phosphate group | | 19.5 | 1.178 ± 0.066 | 19.84 | *<0.01 |
| Phillygenin group | | 13.0 | 1.302 ± 0.046 | 12.51 | *<0.05 |
| Phillygenin ibuprofen ester | High dosage group | 13.0 | 1.147 ± 0.048 | 22.94 | *<0.01, #<0.05 |
| | Medium dosage group | 8.0 | 1.190 ± 0.061 | 20.05 | *<0.01, #<0.05 |
| | Low dosage group | 4.0 | 1.222 ± 0.040 | 17.90 | *<0.05, >0.05 | compared with the virus control group,
*P < 0.05,
**P0.01;
compared with the phillygenin group,
P < 0.05,
P0.01.

TABLE 1-7

Impact of phillygenin ibuprofen ester on the the lung index and the inhibitive rate of the lung index parainfluenza virus infected mice (n = 3)

| Groups | | Drug dosage (mg/kg/d) | Lung index ($\overline{X} \pm S$) | Lung index Inhibitive rate (%) | P value |
|---|---|---|---|---|---|
| Normal control group | | 0 | 1.305 ± 0.039 | — | |
| Virus control group | | 0 | 1.591 ± 0.065 | — | |
| Ribavirin group | | 58.5 | 1.340 ± 0.069 | 15.76 | *<0.01 |
| Oseltamivir phosphate group | | 19.5 | 1.243 ± 0.052 | 21.85 | *<0.01 |
| Phillygenin group | | 13.0 | 1.357 ± 0.050 | 14.69 | *<0.01 |
| Phillygenin ibuprofen ester | High dosage group | 13.0 | 1.237 ± 0.070 | 22.25 | *<0.01, #<0.05 |
| | Medium dosage group | 6.5 | 1.275 ± 0.061 | 19.89 | *<0.01, #<0.05 |
| | Low dosage group | 3.25 | 1.320 ± 0.053 | 17.01 | *<0.01, >0.05 | compared with the virus group,
*P < 0.05,
**P0.01;
compared with the phillygenin group,
p < 0.05,
P0.01.

② Determination of Virus Hemagglutination Titer of Lung Suspensions

After the mice were infected with the influenza virus and the parainfluenza virus, the virus hemagglutination titers (InX) of lung tissues of the infection model group were 32.40 and 33.11, respectively, after treatment with phillygenin ibuprofen ester of different concentrations for 5 days, both of the virus hemagglutination titers of lung tissues decreased to some extent, and as compared with the infection model group, the difference was significant (P<0.01); therein, the influenza and the parainfluenza virus hemagglutination titers of the high dosage and the medium dosage phillygenin ibuprofen ester groups were both significantly lower than those of the model group, and the inhibitive rates were both higher than those of the phillygenin group, with significant differences (P<0.05, p<0.01). The test results could be seen in Tables 1-8 and 1-9.

TABLE 1-8

Effect of phillygenin ibuprofen ester on hemagglutination titers of lung suspensions of the influenza virus infected mice

| Groups | | Drug dosage (mg/kg/d) | Hemagglutination titer (InX) | Inhibitive rate (%) | P value |
|---|---|---|---|---|---|
| Normal control group | | 0 | 0 | | |
| Virus control group | | 0 | 32.40 ± 1.105 | | |
| Ribavirin group | | 58.5 | 21.91 ± 1.050 | 32.39 | **<0.01 |
| Oseltamivir phosphate group | | 19.5 | 20.50 ± 1.122 | 36.73 | **<0.01 |
| Phillygenin | | 13.0 | 22.61 ± 1.059 | 30.22 | **<0.01 |
| Phillygenin ibuprofen ester | High dosage group | 13.0 | 19.32 ± 0.624 | 40.36 | **<0.01, ##<0.01 |
| | Medium dosage group | 6.5 | 20.50 ± 0.431 | 36.72 | **<0.01, #<0.05 |
| | Low dosage group | 3.25 | 22.01 ± 1.420 | 32.07 | **<0.01, >0.05 | compared with the virus control group,
*P < 0.05,
**P0.01;
compared with the phillygenin group,
p < 0.05,
P0.01.

TABLE 1-9

Effect of phillygenin ibuprofen ester on hemagglutination titers of lung suspensions of the parainfluenza virus infected mice (n = 3)

| group | | Drug dosage (mg/kg/d) | Hemagglutination titer (InX) | Inhibitive rate (%) | P value |
|---|---|---|---|---|---|
| Normal control group | | 0 | 0 | | |
| Virus control group | | 0 | 33.11 ± 1.210 | | |
| Ribavirin group | | 58.5 | 23.22 ± 1.091 | 24.53 | *<0.01 |
| Oseltamivir phosphate group | | 19.5 | 22.05 ± 1.055 | 33.44 | *<0.01 |
| Phillygenin | | 13.0 | 23.79 ± 1.072 | 28.15 | *<0.01 |
| Phillygenin ibuprofen ester group | High dosage group | 13.0 | 19.75 ± 0.902 | 40.34 | *<0.01, #<0.01 |
| | Medium dosage group | 6.5 | 20.75 ± 0.598 | 37.33 | *<0.01, #<0.05 |
| | Low dosage group | 3.25 | 21.55 ± 0.857 | 34.90 | *<0.01, >0.05 | compared with the virus control group,
*P < 0.05,
**P0.01;
compared with the phillygenin group,
p < 0.05,
P0.01.

③ Detection Results of Lung Histology

Microscopically the viral pneumonia model group could be seen that: the interstitial lung, such as bronchi, bronchioles and alveolar walls, of the mice of the influenza and parainfluenza virus induced pneumonia model groups were suffered from congestion, egema, and lymphocytesinfiltration, monomuclear cell infiltration, alveolar wall widening, and inflammatory reaction of pulmonary alveoli. In the high dosage and medium dosage phillygenin ibuprofen ester groups, the lung lesions of mice were significantly alleviated and the lung morphological structure was partially normal. The pathological pictures could be seen in detail in the drawings.

Figure 4:
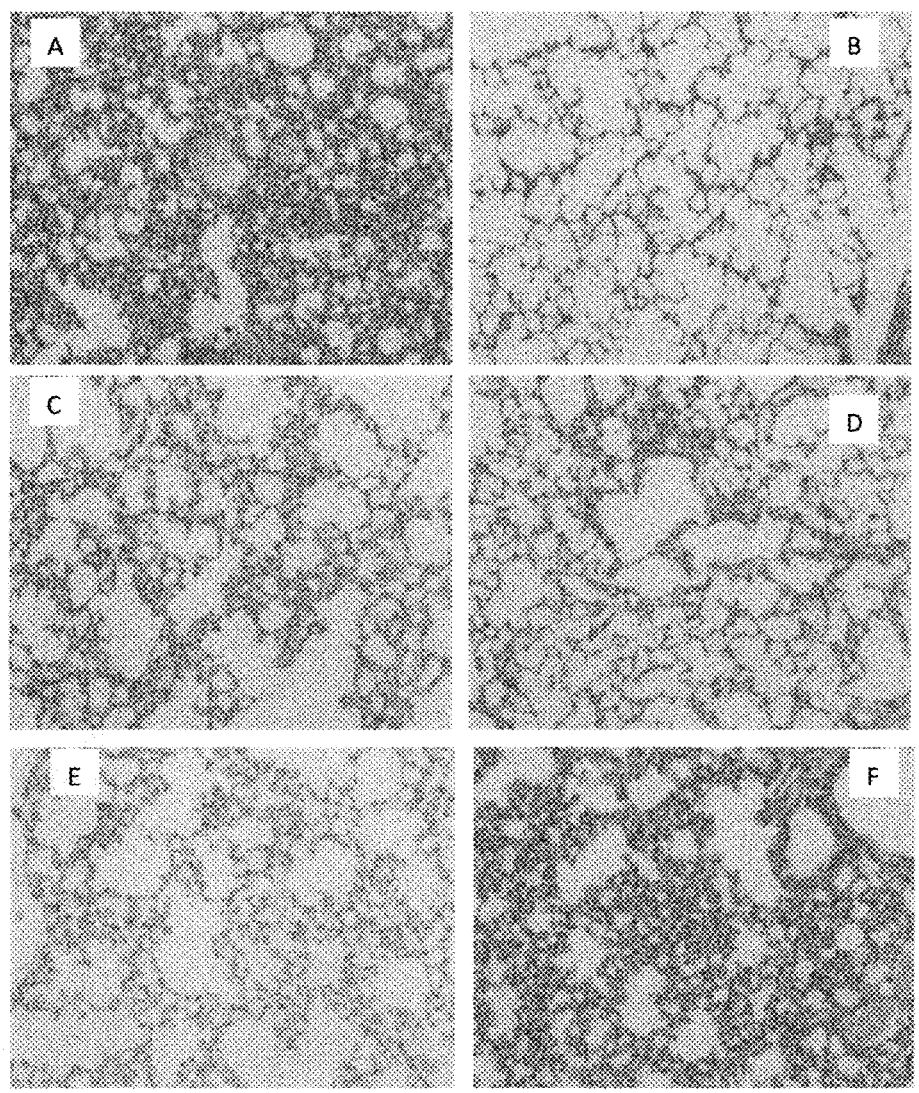
FIG. 4 is pathological sections of the lung tissue of an model mouse infected with influenza virus pneumonia, wherein A is the lung tissue of a normal mouse; B is the lung tissue of a mouse infected with influenza virus pneumonia; C is the lung tissue of a mouse infected with influenza virus pneumonia after the treatment in a high dose group of phillygenin ibuprofen ester; D is the lung tissue of a mouse infected with influenza virus pneumonia after the treatment in a middle dose group of phillygenin ibuprofen ester; E is the lung tissue of a mouse infected with influenza virus pneumonia after the treatment in a low dose group of phillygenin ibuprofen ester; and F is the lung tissue of a mouse infected with influenza virus pneumonia after the treatment by Tamiflu.

The mouse lung tissue pathological slice microscopic examination results of the influenza virus pneumonia model are shown in FIG. 4; FIG. A shows the lung tissue of a normal mouse; FIG. B shows the lung tissue of an influenza virus pneumonia mouse; FIG. C shows the lung tissue of the mouse of the influenza virus pneumonia mouse model after being treated with the high dosage phillygenin ibuprofen ester; FIG. D shows the lung tissue of the mouse of the influenza virus pneumonia mouse model after being treated with the median dosage phillygenin ibuprofen ester; FIG. E shows the lung tissue of the mouse of the influenza virus pneumonia mouse model after being treated with the low dosage phillygenin ibuprofen ester;

FIG. F shows the lung tissue of the mouse of the influenza virus pneumonia mouse model after being treated with Tamiflu.

2.4 Conclusions

The in vivo antiviral test results showed that phillygenin ibuprofen ester in the dosage range of 3.25-13 mg/kg/d has relatively significant inhibition effects on influenza virus and parainfluenza virus as well as the mice viral pneumonia caused thereby at a dosage range of 3.25 mg/kg/d to 13 mg/kg/d, can significantly reduce the lung index and hemagglutination titer thereof, also significantly improve the pulmonary tissue pathology, and have significant difference as compared with the model control group, and the therapeutic effects of the medium-dosage and high-dosage phillygenin ibuprofen ester groups were obviously better than the phillygenin group (*$P<0.05$ or **$P<0.01$), and also showed a trend of being better than the ribavirin and the oseltamivir phosphate groups.

TEST EXAMPLE 2

Test of Antipyretic, Analgesic and Anti-inflammatory Effects of phillygenin ibuprofen ester 1.1 Test Materials (1) Test Animals:

Wistar rats, body weight: 120-250 g, male and female combination, certificate No: Medicinal Animal No. 10-5219; Japanese white rabbits, male, body weight: 1.5-2.0 kg. certificate No.: Medicinal Animal No. 10-5115, all provided by Changchun Gaoxin Medical Animal Experimental Center, animal feeds provided by the Experimental Animal Department of Jilin University.

(2) Test Drug:

phillygenin ibuprofen ester: a white solid (prepared in example 1), produced by Dalian Fusheng Natural Medicine Development Co., Ltd., having a purity of 99.1% as determined by high performance liquid chromatography equipped with both UV detector and evaporative light-scattering detector, through the area normalization method. When used for the test, it was prepared into the desired concentration with 0.5% sodium carboxymethylcellulose.

1.2 Main Equipments and Reagents

YLS-7A rat toe swelling measuring instrument: Equipment Station, Shandong Academy of Medical Services;

722 visible spectrophotometer: manufactured by Shanghai Spectrum Instruments Co., Ltd.;

Portable digital thermodetector: model WSC-411P, the Third Factory of Pudong, Shanghai;

Pilocarpine: Tianjin People's Pharmaceutical Factory, Lot number: 20130112;

Histamine: Shanghai Institute of Biochemistry, Lot number: 20130115;

5-Hyroxytryptamine: Shanghai Institute of Biochemistry, Lot number: 20130623;

Evans blue: Shanghai Chemical Reagent Procurement and Supply Station, Lot number: 20130217;

Chlorpheniramine maleate tablet: Changchun Economic Development Zone Pharmaceutical Co., Ltd., Lot number: 20130801;

Carrageenan: Jilin Drug Research Institute, Lot number: 20130502;

Paracetamol tablet: Liaoyuan Baikang Pharmaceutical Co., Ltd., Lot number: 20130512;

Aspirin tablet: Baicheng Wanda Pharmaceutical Co., Ltd., Lot number: 20130305;

Beer yeast: Beijing AOBOX Biotechnology Co., Ltd., Lot Number: 2013020;

Typhoid and paratyphoid vaccine: Changchun Institute of Biological Products, Lot Number: 20130216.

1.3 Statistical Process

The statistical analysis applies ranksum test, $X^2$ test and t test with two-sample comparison.

2.1 Test of phillygenin ibuprofen ester Effect on Sweat Secretion of Rat Paw Part (Coloring Method)

(1) Material and Method

This test was designed to observe the change of sweat secretion based on the mechanism that sweat gland is distributed on the rat paw pads, and iodine and starch can have purple reaction when encountered with sweat.

In the test, 350 Wistar rats were selected, with equal male and female number, weighing 120-150 g. Such rats were randomly divided into 35 groups by weight and gender, namely 5 groups for the control group (0.5% carboxymethylcellulose), five groups for each dose of the 2.5, 5, and 10 mg/kg phillygenin ibuprofen ester, five groups for ibuprofen (300 mg/kg), five groups for phillygenin (10 mg/kg) and five groups for positive drug pilocarpine (35 mg/kg), with 10 rats for each group. The rats were placed in a self-made rat fixation bag, with the double hind limbs exposed. The dirts on the right paw was gently scrubbed clean with the cotton swab dipped with anhydrous ethanol. Besides that subcutaneous injection was used for the pilocarpine solution, intragastric administration was used for all the other groups. One hour after the administration (30 min after the administration of the pilocarpine group), the original sweat in the right rat paw of each group and the sweat caused by struggling were firstly wiped dry with dry cotton swab, and coated with Hetian-Gao Yuan's reagent A liquid (iodine of 2 g was taken to be dissolved in 100 ml of anhydrous ethanol), and then, after complete dryness, a thin coating of Hetian-Gao Yuan's reagent B liquid (soluble starch of 50 g and castor oil of 100 ml were taken and uniformly mixed) was coated. After coating the B liquid for 1, 5, 10, 15 and 20 min respectively, magnifying glass was used to carefully observe the color and number of dark purple coloring points (i.e., sweat points). When the test was complete, statistical process was carried out according to the rank-sum test with two-sample comparison, in order to compare the difference between the groups.

(2) Result

Compared with the control group, obvious promoting effect was observed for the phillygenin ibuprofen ester group of 10 mg/kg on the sweat secretion of rat paw part after coating B liquid for 5, 10, 15 and 20 min (*$P<0.05$), and it had the effect characteristic of promoting the sweat secretion of rat paw part, which was equivalent to the positive drug pilocarpine; therein, the phillygenin ibuprofen ester of high, medium and low doses showed significant effect on promoting the rat foot paw sweat secretion after 5 to 20 minutes, 10 to 20 minutes, and 20 minutes of the administration, respectively; the phillygenin ibuprofen ester of high and medium doses had a better therapeutic effect for promoting sweating after 5 to 20 minutes and 10 to 15 minutes of the administration than phillygenin (#$P<0.05$), while the high dose had a better therapeutic effect for promoting sweating after 20 minutes of the administration than ibuprofen. See Tables 2-1, 2-2, 2-3, 2-4 and 2-5.

TABLE 2-1

Test of phillygenin ibuprofen ester effect on sweat secretion of rat paw part (coloring method)

| Groups | Animal number | Animal number of sweat points of each level after coating B liquid for 1 minute | | | | | P value |
|---|---|---|---|---|---|---|---|
| | | − | + | ++ | +++ | ++++ | |
| Control group Ibuprofen group | 10 | 2 | 2 | 3 | 2 | 1 | >0.05 |
| 300.0 mg/kg Phillygenin group | 10 | 0 | 1 | 3 | 1 | 5 | >0.05 |
| 10.0 mg/kg Pilocarpine | 10 | 0 | 3 | 3 | 1 | 3 | >0.05 |
| 35.0 mg/kg Phillygenin ibuprofen ester | 10 | 0 | 1 | 3 | 1 | 5 | >0.05 |
| 2.5 mg/kg | 10 | 0 | 2 | 3 | 3 | 2 | >0.05 |
| 5.0 mg/kg | 10 | 0 | 1 | 2 | 3 | 4 | >0.05 |
| 10.0 mg/kg | 10 | 0 | 1 | 3 | 1 | 5 | >0.05 |

TABLE 2-2

Test of phillygenin ibuprofen ester effect on sweat secretion of rat paw part (coloring method)

| Groups | Animal number | Animal number of sweat points of each level after coating B liquid for 5 minutes | | | | | P value |
|---|---|---|---|---|---|---|---|
| | | − | + | ++ | +++ | ++++ | |
| Control group Ibuprofen group | 10 | 0 | 4 | 1 | 4 | 1 | >0.05 |
| 300.0 mg/kg Phillygenin | 10 | 0 | 2 | 1 | 2 | 5 | <0.05 |
| 10.0 mg/kg Pilocarpine | 10 | 0 | 3 | 2 | 2 | 3 | >0.05 |
| 35.0 mg/kg Phillygenin ibuprofen ester | 10 | 0 | 1 | 2 | 1 | 6 | <0.05 |
| 2.5 mg/kg | 10 | 0 | 1 | 3 | 3 | 3 | >0.05 |
| 5.0 mg/kg | 10 | 0 | 1 | 4 | 1 | 5 | >0.05 |
| 10.0 mg/kg | 10 | 0 | 0 | 3 | 2 | 5 | *<0.05, #<0.05 |

TABLE 2-3

Test of phillygenin ibuprofen ester effect on sweat secretion of normal rat paw part (coloring method)

| Groups | Animal number | Animal number of sweat points of each level after coating B liquid for 10 minutes | | | | | P value |
|---|---|---|---|---|---|---|---|
| | | − | + | ++ | +++ | ++++ | |
| Control group Ibuprofen group | 10 | 0 | 3 | 2 | 4 | 1 | >0.05 |
| 300.0 mg/kg Phillygenin | 10 | 0 | 1 | 2 | 2 | 5 | <0.05 |
| 10.0 mg/kg Pilocarpine | 10 | 0 | 1 | 3 | 3 | 3 | >0.05 |
| 35.0 mg/kg Phillygenin ibuprofen ester | 10 | 0 | 1 | 2 | 1 | 6 | <0.05 |
| 2.5 mg/kg | 10 | 0 | 1 | 2 | 3 | 4 | >0.05 |
| 5.0 mg/kg | 10 | 0 | 0 | 3 | 2 | 5 | *#<0.05 |
| 10.0 mg/kg | 10 | 0 | 0 | 2 | 3 | 5 | *#<0.05 |

TABLE 2-4

Test of phillygenin ibuprofen ester effect on sweat secretion of normal rat paw part (coloring method)

| Groups | Animal number | Animal number of sweat points of each level after coating B liquid for 15 minutes | | | | | P value |
|---|---|---|---|---|---|---|---|
| | | − | + | ++ | +++ | ++++ | |
| Control group Ibuprofen group | 10 | 0 | 3 | 2 | 4 | 1 | >0.05 |
| 300.0 mg/kg Phillygenin | 10 | 0 | 1 | 2 | 2 | 5 | <0.05 |
| 10.0 mg/kg Pilocarpine | 10 | 0 | 1 | 2 | 3 | 4 | >0.05 |
| 35.0 mg/kg Phillygenin ibuprofen ester | 9 | 0 | 0 | 2 | 1 | 6 | <0.05 |
| 2.5 mg/kg | 10 | 0 | 1 | 3 | 1 | 5 | >0.05 |
| 5.0 mg/kg | 10 | 0 | 0 | 2 | 3 | 5 | *#<0.05 |
| 10.0 mg/kg | 10 | 0 | 0 | 1 | 4 | 5 | *#<0.05 |

TABLE 2-5

Test of phillygenin ibuprofen ester effect on sweat secretion of rat paw part (coloring method)

| Groups | Animal number | Animal number of sweat points of each level after coating B liquid for 15 minutes | | | | | P VALUE |
|---|---|---|---|---|---|---|---|
| | | − | + | ++ | +++ | ++++ | |
| Control group | 10 | 0 | 3 | 2 | 4 | 1 | >0.05 |
| Ibuprofen (300.0 mg/kg) | 10 | 0 | 1 | 2 | 2 | 5 | <0.05 |

TABLE 2-5-continued

Test of phillygenin ibuprofen ester effect on sweat
secretion of rat paw part (coloring method)

| Groups | Animal number | Animal number of sweat points of each level after coating B liquid for 15 minutes | | | | | P VALUE |
|---|---|---|---|---|---|---|---|
| | | − | + | ++ | +++ | ++++ | |
| Phillygenin 10.0 mg/kg | 10 | 0 | 1 | 2 | 2 | 5 | <0.05 |
| Pilocarpine (35.0 mg/kg) | 9 | 0 | 0 | 2 | 1 | 6 | <0.05 |
| Phillygenin ibuprofen ester | | | | | | | |
| 2.5 mg/kg | 10 | 0 | 0 | 2 | 3 | 5 | <0.05 |
| 5.0 mg/kg | 10 | 0 | 0 | 1 | 4 | 5 | <0.05 |
| 10.0 mg/kg | 10 | 0 | 0 | 0 | 5 | 5 | *#▲<0.05 |

Level evaluation standard of sweat points:
"−" no sweat point on rat paw pad surface;
"+" sweat point occasionally observed on rat paw pad surface, with sweat area of below about 10% of the paw surface;
"++" sweat points dispersed on rat paw pad surface, with sweat area of about 11-40% of the paw surface;
"+++" sweat points dispersed on rat paw pad surface, with sweat area of about 41-70% of the paw surface;
"++++" sweat points evenly distributed on rat paw pad surface, with sweat area of over 71% of the paw surface.

Comparison between each test group and the control group, *P<0.05; comparison between Phillygenin ibuprofen ester and phillygenin, #P<0.05. Comparison between Phillygenin ibuprofen ester and ibuprofen, ▲P<0.05.

2.2 Test of phillygenin ibuprofen ester Effect on Sweat Secretion of Rat Paw Part (Tissue Morphology Observation Method)

(1) Material and Method

This test was based on the mechanism that when rat sweat gland is excited, in addition to sweat secretion increase, the morphology of sweat gland epithelial cell is also changed. The number increase and expansion of empty cells of the sweat gland epithelial cells can be seen under the optical microscope. Such enlarged vacuole presents mitochondrial in sweat gland epithelial cells swelling, rupture, fusion and secretory vesicle enlargement under the electron microscope, and through the morphological observation of the sweat gland epithelial cell at the rat paw part, the secretory activity of the sweat gland can be known.

In the test, 70 Wistar rats were selected, with equal male and female number, weighing 120-160 g. Such rats were randomly divided into 7 groups by weight and gender, namely the blank control (0.5% carboxymethylcellulose) group, the 2.5, 5, and 10 mg/kg phillygenin ibuprofen ester groups, the ibuprofen group (300 mg/kg), the phillygenin group (10 mg/kg) and the positive drug pilocarpine (35 mg/kg) group, with 10 rats for each group.

Besides that subcutaneous injection was used for the pilocarpine solution, intragastric administration was used for all the other groups. One hour after administration of phillygenin ibuprofen ester (30 min after administration of pilocarpine), the right hind limb was instantly cut off at the ankle joint to immediately take down the pad of the right hind limb and place in a 10% formaldehyde solution, and conventional method was used for fixation, dehydration, embedding, slicing and HE staining. The change in sweat gland epithelial cells at the rat toe part of each group was observed under the optical microscope, to mainly observe the vacuole occurrence rate (i.e. void fraction, percentage of vacuole occurrence=number of sweat glands of vacuole/number of sweat glands observed×100%), and compare the difference between the groups through $X^2$ test for statistical analysis.

(2) Result

Compared with the control group, obvious promoting effect was observed on the sweat secretion of the rat toe part by the phillygenin ibuprofen ester groups of 5 and 10 mg/kg (p<0.01 or p<0.001), see Table 2-6.

TABLE 2-6

Test of phillygenin ibuprofen ester effect on sweat secretion of rat toe part (tissue morphology observation method)

| Groups | Animal number | Number of sweat glands observed | Number of sweat glands of vacuole | Void fraction (%) |
|---|---|---|---|---|
| Control group | 10 | 242 | 14 | 5.78 |
| Ibuprofen (300.0 mg/kg) | 10 | 208 | 57 | 27.40*** |
| Phillygenin (10.0 mg/kg) | 10 | 211 | 23 | 10.90 |
| Pilocarpine (35.0 mg/kg) | 10 | 208 | 57 | 27.40*** |
| Phillygenin ibuprofen ester | | | | |
| 2.5 mg/kg | 10 | 236 | 20 | 8.47 |
| 5.0 mg/kg | 10 | 218 | 42 | 32.11***; # |
| 10.0 mg/kg | 10 | 213 | 75 | 35.21***; ## |

Compared with the control group,
**p < 0.01,
***p < 0.001;
compared with the phillygenin group,
p < 0.05,
p < 0.01.

2.3 Effect of phillygenin ibuprofen ester on Beer Yeast Induced Rat Fever (1) Material and Method Male Wistar rats were selected, weighing 180-200 g. Before the test, WSC-411P portable digital thermometer was used to measure the normal rectal temperature twice (with certain interval for each time), and the average value of the two measurements was taken as the normal body temperature of the rat. Then 70 rats with the body temperature between 36.5° C. and 38° C. were chosen to be randomly divided into 7 groups by weight: the model (0.5% carboxymethylcellulose) group, the 2.5, 5, and 10 mg/kg phillygenin ibuprofen ester groups, the positive drug paracetamol (100 mg/kg) group, the ibuprofen group (i.e. prodrug control group, 300 mg/kg), the phillygenin group (100 mg/kg), with 10 rats for each group. Each group of rats were subjected to back subcutaneous injection with 10% fresh beer yeast suspension of 10 ml/kg to induce heat. After administration of 10% fresh beer yeast suspension for 6.0 h, phillygenin ibuprofen ester and paracetamol were both subjected to intragastric administration, and the model group was intragastrically administrated with equal volume of 0.5% carboxymethylcellulose. Rectal temperature was measured after 1 h, 2 h, 3 h and 4 h of the administration respectively. Changes in the body temperature were observed and difference between the groups was compared by inter-group t test processing through antipyretic percentage.

$$\text{Antipyretic percentage} = \frac{\text{Body temperature at a certain time after administration} - \text{body temperature at 6 h after induced fever}}{\text{Body temperature at 6 h after induced fever}} \times 100\%$$

(2) Result

After subcutaneous injection of 10% fresh beer yeast suspension in the rats of each group for 6 h, the body temperature increased by about 1.5° C., which was significantly different from that before the induced fever ($p<0.001$), indicating that the model of beer yeast causing the rat fever was successfully established. Compared with the model group, the medium and high dose groups (5, 10 mg/kg) of phillygenin ibuprofen ester had significant cooling effects on the rat fever induced by beer yeast suspension after 1 h, 2 h, 3 h and 4 h of the administration ($p<0.05$, or $p<0.01$, $P<0.001$); Compared with the phillygenin and ibuprofen group, the high dose group (10 mg/kg) of phillygenin ibuprofen ester had significant cooling effect on the rat fever induced by beer yeast suspension after 1 h, 2 h, 3 h and 4 h of the administration, and the said significant cooling effect was obviously better than phillygenin ($p<0.01$ or $P<0.001$) and ibuprofen ($p<0.05$ or $p<0.01$); The medium dose group (5 mg/kg) of phillygenin ibuprofen ester had significant cooling effect on the induced rat fever by beer yeast suspension after 1 h, 2 h, 3 h and 4 h of the administration, and the said cooling effect was obviously better than phillygenin ($p<0.05$ or $p<0.01$); the medium dose group (5 mg/kg) of phillygenin ibuprofen ester had significant cooling effect on the induced rat fever by beer yeast suspension after 2 h, 3 h and 4 h of the administration, and the said cooling effect was obviously better than the ibuprofen group ($p<0.05$). The above test results showed that the cooling and antipyretic therapeutic effect of the phillygenin ibuprofen ester compound was significantly better than its precursor compounds of forsythiasin and ibuprofen; The above test results can be seen in Table 2-7.

2.4 Effect of phillygenin ibuprofen ester on Rabbit Fever Induced by Typhoid and Paratyphoid Vaccine (1) Material and Method Japanese male big-ear white rabbits, weighing 1.5-2.0 kg. Before the test, WSC-411P portable digital thermometer was used to measure the normal rectal temperature twice (with certain interval for each time), and the average value was taken as the normal body temperature. Then 48 Japanese big-ear white rabbits with body temperature of 38-39.6° C. were selected and randomly divided into 8 groups by weight, namely: the blank control (normal saline) group, the model control (0.5% carboxymethylcellulose) group, the ibuprofen group (300 mg/kg), the phillygenin group (10 mg/kg), the 1.25, 2.5, and 5 mg/kg phillygenin ibuprofen ester groups and the positive drug paracetamol (50 mg/kg) group. The rabbits were fixed in a fixator. The blank control group was intravenously injected with normal saline of 1 ml/kg via the ear margin; The model control group and the drug groups were intravenously injected with typhoid and paratyphoid vaccines of 0.8 ml/kg via the ear margin. When the body temperature rise of the rabbits was greater than 1° C. (requiring about 1-1.5 h, which was restricted to 1 h in this test), the blank control group and the model group were administered intragastrically with 0.5% carboxymethycellulose of 1 ml/kg, and the drug groups were administered intragastrically with phillygenin ibuprofen ester and paracetamol.

The rectal temperature was measured after administration for 30, 60, 90, 120, 180 and 240 min to observe the changes in the body temperature, and difference between the groups was compared by inter-group t test processing through antipyretic percentage.

$$\text{Antipyretic percentage} = \frac{\begin{array}{c}\text{Body temperature at a certain time after administration} -\\ \text{body temperature at 1 h after inducedfever}\end{array}}{\text{Body temperature at 1 h after inducedfever}} \times 100\%$$

(2) Result

After intravenous injection with the typhoid and paratyphoid vaccines via the ear margin of rabbits for 1 h, the body temperature rise was about 1° C., which indicated that the typhoid and paratyphoid vaccines could be used to prepare the rabbit fever model. Compared with the blank control group, the body temperature of the model group increased continuously during the observation period of 300 min ($p<0.05$-$p<0.001$); compared with the model group, the high and medium dose groups (5, 10 mg/kg) of phillygenin ibuprofen ester after administration for 30-240 min and the low dose group (5 mg/kg) after administration for 60-240 min had significant antipyretic effect for rabbit fever induced by the typhoid and paratyphoid vaccines ($p<0.05$-$p<0.001$); the high and medium dose groups (5, 10 mg/kg) of phillygenin ibuprofen ester after administration for 30-240 min and the low dose group (5 mg/kg) after administration for 60-240 min had significant antipyretic effect on rabbit fever induced by the typhoid and paratyphoid vaccines, which was obviously better than the group of the precursor compound of phillygenin ($p<0.05$-$p<0.001$); the high and medium dose groups (10 mg/kg) of phillygenin ibuprofen ester after administration for 60-240 min had significant antipyretic effect on rabbit fever induced by the typhoid and paratyphoid vaccines, which was obviously better than the ibuprofen group ($p<0.05$ or $p<0.01$); The above test results can be seen in Table 2-8.

2.5 Analgesic Pain Test of phillygenin ibuprofen ester (1) Material and Method

72 Kunming mice were randomly divided into 6 groups, with 12 mice for each group. ① the blank normal control group (i.e. saline group, 10 mg/kg); ② positive drug aspirin group (200 mg/kg); ③ ibuprofen group (300 mg/kg); ④ high dose group of phillygenin ibuprofen ester (300 mg/kg); ⑤ medium dose group of phillygenin ibuprofen ester (150 mg/kg); ⑥ low dose group of phillygenin ibuprofen ester (75 mg/kg). After drug of each group was intragastric administrated for 1 h, the mice were administered intraperitoneally with 0.7% acetic acid solution (10 ml/kg). The number of mice writhings within 15 min after administration was recorded. The number of writhings was taken as the evaluation index to evaluate the analgesic effect.

(2) Result

The analgesic effect of phillygenin ibuprofen ester on mice pain induced by acetic acid can be seen in Table 5. Comparing the low, medium and high dose groups of phillygenin ibuprofen ester with the blank control group (normal saline), significant difference was observed ($P<0.01$), indicating that all different dose groups of phillygenin ibuprofen ester had analgesic effect. Therein, the analgesic therapeutic effect of high dose phillygenin ibuprofen ester was outstanding, better than the positive drug aspirin and the prodrug ibuprofen; See Table 2-9 for details.

TABLE 2-9

Effect of phillygenin ibuprofen ester on mice pain induced by miscount

| Groups | Dose (mg/kg) | Writhing times |
|---|---|---|
| Blank control group | 0 | 58.2 |
| Positive drug group (aspirin) | 200 | 5.0* |
| Prodrug (ibuprofen) | 300 | 9.7* |

TABLE 2-9-continued

Effect of phillygenin ibuprofen ester
on mice pain induced by miscount

| Groups | Dose (mg/kg) | Writhing times |
|---|---|---|
| Phillygenin ibuprofen ester | | |
| High dose group | 300 | 3.9*# |
| Medium dose group | 150 | 6.5* |
| Low dose group | 75 | 15.8* | compared with the blank control group,
*P < 0.01;
compared with different dose groups of ibuprofen,
P < 0.01.

2.6 Effect of phillygenin ibuprofen ester on Rat Toe Swelling Induced by Carrageenan
(1) Material and Method 70 Male Wistar rats with body weight of 120-150 g were selected to be randomly divided into 7 groups by weight, i.e.: the blank control (0.5% carboxymethylcellulose) group, the 2.5, 5, and 10 mg/kg phillygenin ibuprofen ester groups, the prodrug ibuprofen (300 mg/kg) group, the phillygenin group (10 mg/kg) and the positive drug aspirin (200 mg/kg) group, with 10 rats for each group. The test groups were administered by sublingual intravenous injection. Before the test, capillary magnification measurement method was used to measure the normal volume of the right hind foot of the rats in each group. To avoid errors, the measurement location was fixed and the operation was made by one person both before and after the administration. The average value of the two measurements was taken as the normal volume of the right hind foot of the rats before administration. After the administration, 1% carrageenan of 0.1 ml was immediately subcutaneously injected at the paw of the right hind foot of the rat to induce inflammation. The volume of the right paw at 15, 30, 60, 120, 180, 240, 300 and 360 min after the induced inflammation was measured. The difference between the groups was compared by inter-group t test processing through the difference percentage (swelling ratio) of the paw volume before and after the induced rat inflammation.

Swelling ratio (%) =

$$\frac{\text{Paw volume of the right hind foot after the induced inflammation} - \text{Paw volume of the right hind foot before administration}}{\text{Paw volume of the right hind foot before administration}} \times 100\%$$

Result

Compared with the blank control group, the high dose group of phillygenin ibuprofen ester had significant inhibitive effects ($p<0.05$-$p<0.001$) on the rat paw swelling induced by carrageenin within 30 min to 360 min after administration, which was obviously better than the prodrug phillygenin ($p<0.05$-$p<0.001$), and the therapeutic effect at 30 min after administration was obviously better than the prodrug ibuprofen ($p<0.05$); The medium dose group of phillygenin ibuprofen ester had significant inhibitive effects ($p<0.05$-$p<0.01$) for the rat paw swelling induced by carrageenin within 30 min to 240 min after administration, its therapeutic effect at 30 min-120 min after administration was obviously better than the prodrug phillygenin, and the therapeutic effect at 240 min after administration was obviously better than the prodrug ibuprofen. The present test results demonstrated that phillygenin ibuprofen ester has comparatively obvious anti-inflammatory effect, and its therapeutic effect is better than the prodrugs of phillygenin and ibuprofen. See Table 2-10.

TABLE 2-7

Impact of phillygenin ibuprofen ester on rat ferver caused by beer yeast ($\bar{\chi} \pm s$, n = 10)

| Groups | Normal | after the induced fever 6.0 h | Body temperature (° C.) Time after administration (h) 1 | 2 |
|---|---|---|---|---|
| Model control group | 37.72 ± 0.90 | 39.30 ± 0.54 | 39.44 ± 0.58 | 39.42 ± 0.47 |
| (%) | | 4.22 ± 2.11### | 0.37 ± 1.66 | 0.31 ± 1.77 |
| Paracetamol (100 mg/kg) | 37.55 ± 0.70 | 39.48 ± 0.62 | 38.66 ± 0.58 | 38.19 ± 0.59 |
| (%) | | 5.14 ± 1.42### | −2.07 ± 0.54** | −3.27 ± 0.77*** |
| Ibuprofen (300 mg/kg) | 37.66 ± 0.70 | 39.63 ± 0.32 | 39.21 ± 0.11 | 38.92 ± 0.35 |
| (%) | | 5.22 ± 1.42### | −1.05 ± 0.54* | −1.7 ± 0.77* |
| Phillygenin (10.0 mg/kg) | 37.52 ± 0.56 | 39.44 ± 0.69 | 39.40 ± 0.43 | 39.20 ± 0.52 |
| (%) | | 5.13 ± 1.45### | −0.09 ± 1.11 | −0.61 ± 1.67 |
| Phillygenin ibuprofen ester | | | | |
| 2.5 mg/kg | 37.33 ± 0.56 | 39.33 ± 0.69 | 38.93 ± 0.43 | 38.75 ± 0.43 |
| (%) | | 5.36 ± 1.40### | −1.01 ± 1.05*▲ | −1.48 ± 1.11*▲ |
| 5.0 mg/kg | 37.39 ± 0.53 | 39.23 ± 0.43 | 38.48 ± 0.59 | 38.33 ± 0.50 |
| (%) | | 4.92 ± 1.28### | −1.91 ± 0.40*▲ | −2.29 ± 0.54**△▲▲ |
| 10.0 mg/kg | 37.53 ± 0.55 | 39.44 ± 0.63 | 38.61 ± 0.51 | 39.13 ± 0.45 |
| (%) | | 5.10 ± 1.57### | −2.10 ± 0.53**△▲▲ | −3 33 ± 0 98***△△▲▲▲ |

TABLE 2-7-continued

Impact of phillygenin ibuprofen ester on rat ferver caused by beer yeast ($\bar{\chi} \pm s$, n = 10)

| Groups | Body temperature (° C.) Time after administration (h) | |
|---|---|---|
| | 3 | 4 |
| Model control group | 38.88 ± 0.46 | 38.57 ± 0.49 |
| (%) | −1.07 ± 1.54 | −1.86 ± 1.20 |
| Paracetamol (100 mg/kg) | 37.98 ± 0.19 | 37.84 ± 0.32 |
| (%) | −3.80 ± 1.43*** | −4.15 ± 1.59*** |
| Ibuprofen (300 mg/kg) | 38.71 ± 0.20 | 38.49 ± 0.51 |
| (%) | −2.32 ± 1.41** | −2.88 ± 1.50** |
| Phillygenin (10.0 mg/kg) | 38.81 ± 0.37 | 38.67 ± 0.58 |
| (%) | −1.59 ± 1.70* | −1.95 ± 1.14* |
| Phillygenin ibuprofen ester | | |
| 2.5 mg/kg | 38.56 ± 0.52 | 38.25 ± 0.58 |
| (%) | −1.97 ± 1.67* | −2.47 ± 1.80** |
| 5.0 mg/kg | 37.85 ± 0.33 | 37.67 ± 0.45 |
| (%) | −3.52 ± 0.38***△▲ | −3.98 ± 0.52***△▲▲ |
| 10.0 mg/kg | 37.8 ± 0.40 | 37.74 ± 0.31 |
| (%) | −4.01 ± 1.12***△▲▲ | −4.30 ± 1.26***△▲▲ |

Compared with the normal one (before the induced fever) ###$p < 0.001$
Compared with the model control group, *$P < 0.05$, $P < 0.01$, *$P < 0.001$
Compared with the phillygenin ibuprofen ester and ibuprofen group, △$P < 0.05$, △△$P < 0.01$
Compared with the phillygenin ibuprofen ester and phillygenin group, ▲$P < 0.05$, ▲▲$P < 0.01$, ▲▲▲$P < 0.001$

TABLE 2-8

Effect of phillygenin ibuprofen ester on rabbit fever body temperature caused by the typhoid and paratyphoid vaccines ($\bar{\chi} \pm s$, n = 6)

| Groups | Normal | after the induced fever 1.0 h | Body temperature (° C.) Time after administration (h) | | |
|---|---|---|---|---|---|
| | | | 30 | 60 | 90 |
| Blank control group | 39.47 ± 0.21 | 39.50 ± 0.24 | 39.56 ± 0.23 | 39.45 ± 0.24 | 39.54 ± 0.25 |
| (%) | | 0.15 ± 0.20 | 0.15 ± 0.20 | −0.13 ± 0.16 | 0.11 ± 0.15 |
| Model control group | 39.68 ± 0.53 | 41.10 ± 0.53 | 41.23 ± 0.53 | 41.27 ± 0.51 | 41.22 ± 0.51 |
| (%) | | 3.60 ± 1.08#### | 0.32 ± 0.25 | 0.41 ± 0.18## | 0.28 ± 0.10# |
| Paracetamol (50 mg/kg) | 39.53 ± 0.40 | 40.09 ± 0.45 | 40.53 ± 0.68 | 40.10 ± 0.48 | 39.83 ± 0.57 |
| (%) | | 3.71 ± 0.28#### | −1.14 ± 0.59* | −2.18 ± 0.16** | −2.83 ± 0.16*** |
| Ibuprofen (300 mg/kg) | 39.62 ± 0.37 | 41.11 ± 0.38 | 40.74 ± 0.52 | 40.56 ± 0.40 | 40.07 ± 0.44 |
| (%) | | 3.75 ± 0.21#### | −0.90 ± 0.41* | −1.35 ± 0.11* | −2.52 ± 0.13** |
| Phillygenin (10.0 mg/kg) | 39.50 ± 0.21 | 41.04 ± 0.49 | 41.15 ± 0.47 | 40.83 ± 0.45 | 40.67 ± 0.30 |
| (%) | | 3.90 ± 0.50#### | 0.28 ± 0.19 | −0.50 ± 0.18 | −0.91 ± 0.22* |
| Phillygenin ibuprofen ester | | | | | |
| 1.25 mg/kg | 39.50 ± 0.29 | 41.08 ± 0.42 | 40.68 ± 0.41 | 40.61 ± 0.38 | 40.50 ± 0.39 |
| (%) | | 3.99 ± 0.55#### | 0.98 ± 0.11 | −1.15 ± 0.15*▲ | −1.40 ± 0.20* |
| 2.5 mg/kg | 39.78 ± 0.26 | 41.28 ± 0.32 | 40.83 ± 0.39 | 40.37 ± 0.33 | 40.12 ± 0.21 |
| (%) | | 3.79 ± 0.45#### | −1.10 ± 0.00*▲ | −2.20 ± 0.05**△△▲ | −2.81 ± 0.12***▲▲▲ |
| 5.0 mg/kg | 39.72 ± 0.36 | 41.11 ± 0.26 | 40.57 ± 0.28 | 40.04 ± 0.20 | 39.88 ± 0.23 |
| (%) | | 3.51 ± 0.43#### | −1.30 ± 0.11*▲ | −2.61 ± 0.10**△△▲▲ | −2.98 ± 0.22***▲▲▲ |

TABLE 2-8-continued

Effect of phillygenin ibuprofen ester on rabbit fever body temperature caused by the typhoid and paratyphoid vaccines ($\bar{\chi} \pm s$, n = 6)

| Groups | Body temperature (° C.) Time after administration (h) | | |
|---|---|---|---|
| | 120 | 180 | 240 |
| Blank control group | 39.49 ± 0.27 | 39.56 ± 0.23 | 39.59 ± 0.25 |
| (%) | −0.02 ± 0.19 | 0.15 ± 0.23 | 0.23 ± 0.05 |
| Model control group | 41.21 ± 0.54 | 40.95 ± 0.47 | 40.49 ± 0.59 |
| (%) | 0.26 ± 0.21# | −0.36 ± 0.21# | −1.48 ± 0.24### |
| Paracetamol (50 mg/kg) | 39.72 ± 0.54 | 39.61 ± 0.48 | 39.53 ± 0.46 |
| (%) | −3.11 ± 0.29*** | −3.38 ± 0.25*** | −3.58 ± 0.36*** |
| Ibuprofen (300 mg/kg) | 39.88 ± 0.55 | 39.77 ± 0.53 | 39.63 ± 0.41 |
| (%) | −3.00 ± 0.23*** | −3.25 ± 0.29*** | −3.60 ± 0.32*** |
| Phillygenin (10.0 mg/kg) | 40.47 ± 0.49 | 40.29 ± 0.31 | 40.19 ± 0.33 |
| (%) | −1.40 ± 0.30** | −1.82 ± 0.46** | −2.07 ± 0.21* |
| Phillygenin ibuprofen ester | | | |
| 1.25 mg/kg | 40.29 ± 0.42 | 40.10 ± 0.35 | 39.89 ± 0.39 |
| (%) | −1.92 ± 0.31**▲ | −2.39 ± 0.43*** | −2.89 ± 0.23***▲ |
| 2.5 mg/kg | 40.02 ± 0.20 | 39.90 ± 0.25 | 39.79 ± 0.29 |
| (%) | −3.06 ± 0.43***▲▲ | −3.35 ± 0.29***▲▲ | −3.60 ± 0.36***▲▲ |
| 5.0 mg/kg | 39.65 ± 0.20 | 39.42 ± 0.25 | 39.17 ± 0.28 |
| (%) | −3.54 ± 0.18***△▲▲▲ | −4.10 ± 0.17***△▲▲ | −4.37 ± 0.15***△▲▲▲ |

Compared with the blank control group, #p < 0.05, ##p < 0.01, ###p < 0.001
Compared with the model control group, *p < 0.05, p < 0.01, *p < 0.001
Comparison between the phillygenin ibuprofen ester group and the ibuprofen group, △P < 0.05; △△P < 0.01
Comparison between the phillygenin ibuprofen ester group and the phillygenin group, ▲P < 0.05, ▲▲P < 0.01, ▲▲▲P < 0.001

TABLE 2-10

Inhibitive effect of phillygenin ibuprofen ester on rat foot swelling induced by carrageenan ($\bar{\chi} \pm s$, n = 10)

| Groups | Swelling ratio (%) | | | |
|---|---|---|---|---|
| | 30 min | 60 min | 120 min | 180 min |
| Blank control group | 0.295 ± 0.101 | 0.350 ± 0.165 | 0.525 ± 0.357 | 0.860 ± 0.331 |
| Aspirin (200 mg/kg) | 0.120 ± 0.138** | 0.168 ± 0.172* | 0.215 ± 0.178* | 0.343 ± 0.337** |
| Ibuprofen (300 mg/kg) | 0.110 ± 0.119** | 0.151 ± 0.172* | 0.210 ± 0.178* | 0.330 ± 0.337** |
| Phillygenin (10.0 mg/kg) | 0.245 ± 0.210 | 0.283 ± 0.176 | 0.360 ± 0.156 | 0.560 ± 0.216* |
| Phillygenin ibuprofen ester | | | | |
| 2.5 mg/kg | 0.215 ± 0.120 | 0.293 ± 1.117 | 0.450 ± 0.254 | 0.800 ± 0.339 |
| 5.0 mg/kg | 0.065 ± 0.112**▲▲ | 0.127 ± 0.178*▲▲ | 0.209 ± 0.438*▲ | 0.338 ± 0.524** |
| 10.0 mg/kg | 0.025 ± 0.210***△▲▲▲ | 0.079 ± 0.156**△▲▲ | 0.140 ± 0.156***▲▲ | 0.191 ± 0.216***▲▲ |

| Groups | Swelling ratio (%) | | |
|---|---|---|---|
| | 240 min | 300 min | 360 min |
| Blank control group | 0.885 ± 0.341 | 1.010 ± 0.410 | 1.065 ± 0.341 |
| Aspirin (200 mg/kg) | 0.470 ± 0.289** | 0.690 ± 0.369 | 0.525 ± 0.338** |
| Ibuprofen (300 mg/kg) | 0.4600 ± 0.289** | 0.681 ± 0.369 | 0.623 ± 0.338** |
| Phillygenin (10.0 mg/kg) | 0.725 ± 0.294 | 0.890 ± 0.226 | 0.875 ± 0.231 |

TABLE 2-10-continued

Inhibitive effect of phillygenin ibuprofen ester on rat foot swelling induced by carrageenan ($\bar{\chi} \pm s$, n = 10)

| Phillygenin ibuprofen ester | | | |
|---|---|---|---|
| 2.5 mg/kg | 0.865 ± 0.303 | 1.045 ± 0.308 | 0.930 ± 0.200 |
| 5.0 mg/kg | 0.461 ± 0.402**△ | 0.688 ± 0.503 | 0.675 ± 0.578 |
| 10.0 mg/kg | 0.255 ± 0.294***▲▲ | 0.310 ± 0.226***△△△ | 0.405 ± 0.231***▲ |

Compared with the blank control group *$P < 0.05$, $P < 0.01$, *$P < 0.001$
Comparison between the phillygenin ibuprofen ester group and the ibuprofen group, △$P < 0.05$, △△$P < 0.01$, △△△$P < 0.001$
Comparison between the phillygenin ibuprofen ester group and the phillygenin group, ▲$P < 0.05$, ▲▲$P < 0.01$, ▲▲▲$P < 0.001$

The invention claimed is:

1. A phillygenin ibuprofen ester compound with a general structural formula as represented by formula (I):

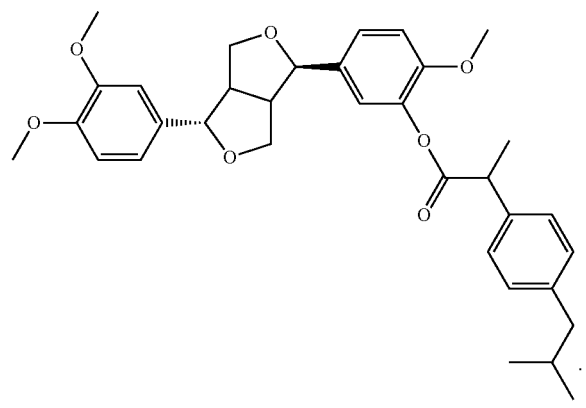 [SMILES: COc1ccc([C@H]2OCC3C2CO[C@H]3c2ccc(OC)c(OC(=O)C(C)c3ccc(CC(C)C)cc3)c2)cc1OC]

(I)

2. A preparation method of the phillygenin ibuprofen ester compound thereof according to claim 1, comprising the following sequentially performed steps:
    A) Ibuprofen is subjected to an acylation reaction with an acylating agent to obtain ibuprofen acyl chloride; and
    B) An esterification reaction is carried out between phillygenin and ibuprofen acyl chloride with the action of a catalyst to obtain the final product.

3. The preparation method according to claim 2, characterized in that the acylating agent in the step A) is selected from the group consisting of thionyl chloride, phosphorus trichloride, phosphorus pentachloride, phosphorus oxychloride, and any combination thereof.

4. The preparation method according to claim 2, characterized in that the catalyst in the step B) is selected from the group consisting of an organic base, an inorganic base, and any combination thereof.

5. The preparation method according to claim 4, characterized in that the inorganic base is selected from the group consisting of sodium carbonate, potassium carbonate, sodium bicarbonate, potassium bicarbonate, and any combination thereof; and the organic base is selected from the group consisting of pyridine, triethylamine, N,N-dimethylformamide, a metal alkoxide, and any combination thereof.

6. The preparation method according to claim 2, characterized in that the molar ratio of phillygenin in the step B) to ibuprofen in the step A) is 0.8-1.2:1.

7. The preparation method according to claim 2, characterized in that the esterification reaction in the step B) is carried out with stirring after phillygenin and ibuprofen acyl chloride are added to an organic solvent.

8. The preparation method according to claim 2, characterized in that further comprises step C, in which the product after the esterification reaction is subjected to the isolation and purification treatment, the reaction solvent is removed from the product after the esterification reaction, and then a solid is subjected to the recrystallization treatment.

9. A method of treating a patient, wherein the method comprises administering to the patient an antiviral composition comprising the phillygenin ibuprofen ester compound of claim 1.

10. A method of preparing a medicine or health care product for treating a viral disease, wherein the method comprises formulating the medicine or health care product with the phillygenin ibuprofen ester compound of claim 1.

11. The method of claim 10, wherein the viral diseases is caused by a virus selected from the group consisting of influenza viruses, parainfluenza viruses, respiratory syncytial viruses (RSV), coxsackievirus A16, and any combination thereof.

12. An antiviral medicine, characterized in that it contains a phillygenin ibuprofen ester.

13. The preparation method according to claim 3, characterized in that the catalyst in the step B) is selected from the group consisting of an organic base, an inorganic base, and any combination thereof.

14. The preparation method according to claim 13, characterized in that the inorganic base is selected from the group consisting of sodium carbonate, potassium carbonate, sodium bicarbonate, potassium bicarbonate, and any combination thereof; and the organic base is selected from the group consisting of pyridine, triethylamine, N,N-dimethylformamide, a metal alkoxide, and any combination thereof.

15. The preparation method according to claim 3, characterized in that the molar ratio of phillygenin in the step B) to ibuprofen in the step A) is 0.8-1.2:1.

16. The preparation method according to claim 3, characterized in that the esterification reaction in the step B) is carried out with stirring after phillygenin and ibuprofen acyl chloride are added to an organic solvent.

17. The preparation method according to claim 3, characterized in that further comprises step C, in which the product after the esterification reaction is subjected to the isolation and purification treatment, the reaction solvent is removed from the product after the esterification reaction, and then a solid is subjected to the recrystallization treatment.

* * * * *